(12) United States Patent
George et al.

(10) Patent No.: US 8,318,789 B2
(45) Date of Patent: Nov. 27, 2012

(54) CO-CRYSTALS OF PROPICONAZOLE

(75) Inventors: Neil George, Huddersfield (GB); James Forrest, Huddersfield (GB); Paul Edward Bonnett, Greensboro, NC (US); Pauline Theresa Gavin, Huddersfield (GB)

(73) Assignee: Syngenta Limited, Guildford, Surrey (GB)

( * ) Notice: Subject to any disclaimer, the term of this patent is extended or adjusted under 35 U.S.C. 154(b) by 381 days.

(21) Appl. No.: 12/532,212

(22) PCT Filed: Mar. 20, 2008

(86) PCT No.: PCT/GB2008/001019
§ 371 (c)(1),
(2), (4) Date: Jan. 15, 2010

(87) PCT Pub. No.: WO2008/117037
PCT Pub. Date: Oct. 2, 2008

(65) Prior Publication Data
US 2010/0179204 A1    Jul. 15, 2010

(30) Foreign Application Priority Data
Mar. 23, 2007 (GB) ................... 0705657.5
Mar. 23, 2007 (GB) ................... 0705659.1

(51) Int. Cl.
*A61K 31/4196* (2006.01)
*C07D 249/08* (2006.01)
(52) U.S. Cl. .................... 514/383; 548/266.6
(58) Field of Classification Search ................ 514/383; 548/266.6
See application file for complete search history.

(56) References Cited

FOREIGN PATENT DOCUMENTS

| EP | 0300413 | 1/1989 |
|---|---|---|
| GB | 1522657 | 8/1978 |
| WO | 9926474 | 6/1999 |
| WO | 199926473 | 6/1999 |

OTHER PUBLICATIONS

Tomlin: "The Pesticide Manual, 10th Ed." 1994, British Crop Protection Council & the Royal Society of Chemistry, XP002483810, pp. 855-857: propiconazole.
Bond: "What is co-crystal?" Cryst Eng Comm, Royal Society of Chemistry, Cambridge, GB, vol. 9, Jul. 11, 2007, pp. 833-834, XP001538430; ISSN: 1466-8033.

*Primary Examiner* — Taofiq A Solola
(74) *Attorney, Agent, or Firm* — R. Kody Jones

(57) ABSTRACT

The present invention relates to co-crystals of propiconazole and a co-crystal forming compound.

12 Claims, 19 Drawing Sheets ically a yellowish, odourless, viscous liquid between −10 and 60° C. It is known to crystallise at room temperature over long periods of time. In addition, due to substantial fluctuations in temperature that may occur during processing and storage of agrochemical formulations, propiconazole may go through cycles of melting and recrystallisation leading to the generation of large and undesirable particles. These particles could, for example, block spray nozzles during application of the product. In addition, such melting and recrystallisation events mean that it is difficult to maintain the product as a homogeneous formulation and this may lead to issues during transfer to dilution tanks and in ensuring the correct concentration on dilution. There is thus a need for new forms of propiconazole that will overcome these problems whilst still retaining its advantageous fungicidal properties.

CO-CRYSTALS OF PROPICONAZOLE

This application is a 371 of International Application No. PCT/GB2008/001019 filed Mar. 20, 2008, which claims priority to GB 0705657.5 filed Mar. 23, 2007, and GB 0705659.1 filed Mar. 23, 2007, the contents of which are incorporated herein by reference.

FIELD OF THE INVENTION

The present invention relates to novel co-crystals of propiconazole and their use in fungicidal compositions, in particular agrochemical compositions.

BACKGROUND OF THE INVENTION

Propiconazole is a fungicide from the triazole group and is a steroid demethylation (ergosterol biosynthesis) inhibitor. It is a systemic foliar fungicide with protective and curative action, with translocation acropetally in the xylem. At labelled application rates, propiconazole controls numerous diseases caused by, for example, *Cochliobolus sativus*, *Erysiphe graminis*, *Leptosphaeria nodorum*, *Puccinia* spp., *Pyrenophora teres*, *Pyrenophora tritici-repentis*, *Rhynchosporium secalis* and *Septoria* spp. on cereals; *Mycosphaerella musicola* and *Mycosphaerella fijiensis* var. *difformis* in bananas; *Sclerotinia homoeocarpa*, *Rhizoctonia solani*, *Puccinia* spp., *Erysiphe graminis* in turf; *Rhizoctonia solani*, *Helminthosporium oryzae* and dirty panicle complex in rice; *Hemileia vastatrix* in coffee; *Cercospora* spp. in peanuts; *Monilinia* spp., *Podosphaera* spp., *Sphaerotheca* spp. and *Tranzschelia* spp. in stone fruit; and *Helminthosporium* spp. in maize. Propiconazole is described in "The Pesticide Manual" [The Pesticide Manual—A World Compendium; Thirteenth Edition; Editor: C. D. S. Tomlin; The British Crop Protection Council] under entry number (675).

Depending on isomeric composition propiconazole is typically a yellowish, odourless, viscous liquid between −10 and 60° C. It is known to crystallise at room temperature over long periods of time. In addition, due to substantial fluctuations in temperature that may occur during processing and storage of agrochemical formulations, propiconazole may go through cycles of melting and recrystallisation leading to the generation of large and undesirable particles. These particles could, for example, block spray nozzles during application of the product. In addition, such melting and recrystallisation events mean that it is difficult to maintain the product as a homogeneous formulation and this may lead to issues during transfer to dilution tanks and in ensuring the correct concentration on dilution. There is thus a need for new forms of propiconazole that will overcome these problems whilst still retaining its advantageous fungicidal properties.

SUMMARY OF THE INVENTION

Accordingly, the present invention provides novel co-crystalline forms of propiconazole with a higher melting point than the commercially available versions of propiconazole. Suitably, the melting point of the co-crystal, measured as a single melting exotherm by differential scanning calorimetry (DSC), is above 50° C. and preferably between 80 and 140° C. More suitably, the melting point is between 100 and 130° C. Most suitably, the melting point is between 125 and 135° C.

DETAILED DESCRIPTION OF THE INVENTION

Figure 1:
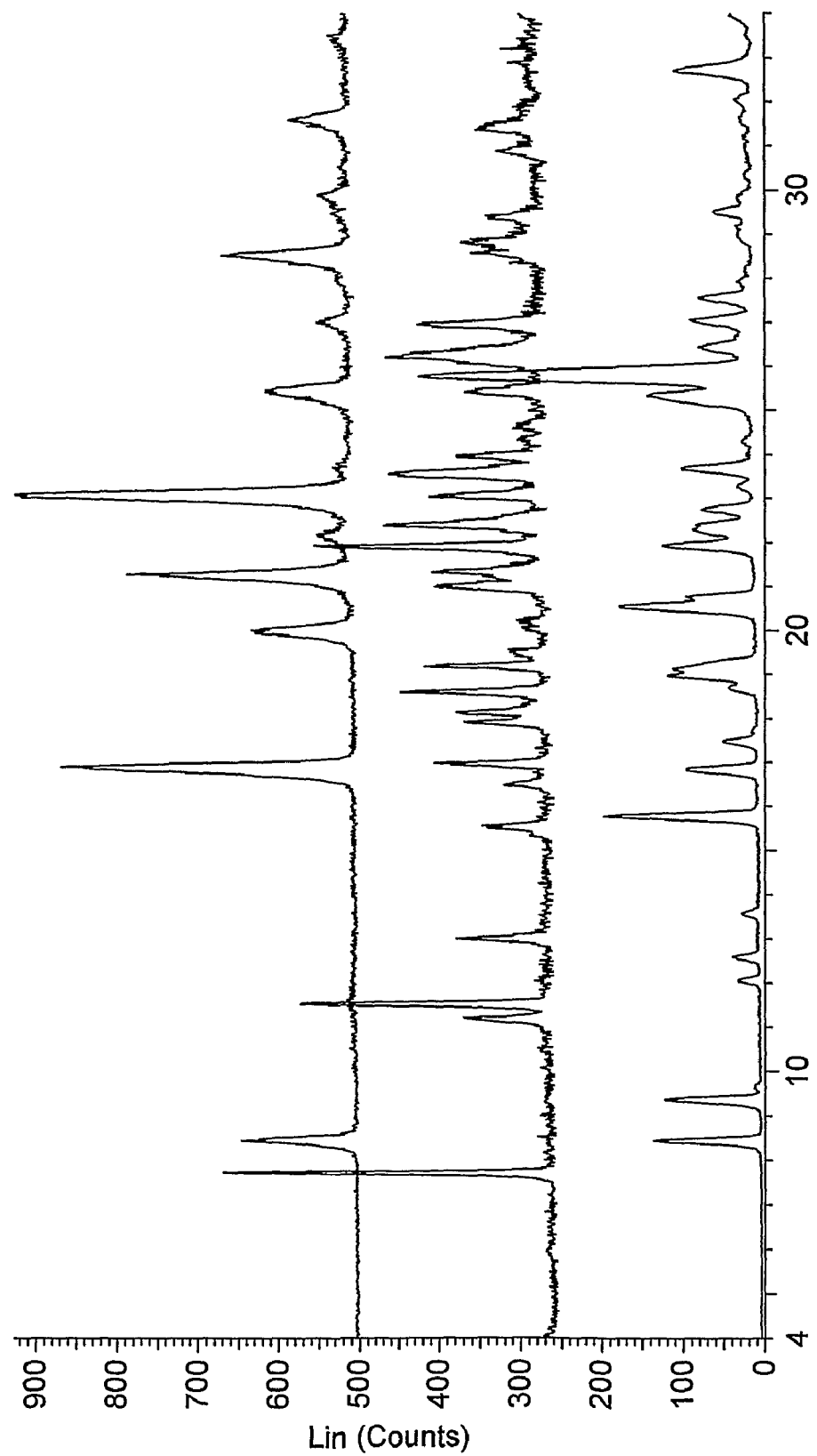
FIG. 1 shows the powder X-Ray diffraction patterns of (a) propiconazole technical grade, (b) propiconazole-4,4'-dihydroxybiphenyl co-crystal and (c) 4,4'-dihydroxybiphenyl.

In particular, the invention provides a co-crystal of propiconazole with a co-crystal forming compound which has at least one functional group selected from hydroxyl (including alcohol and phenol), ketone, carboxylic acid, amide, primary amine, secondary amine, tertiary amine, sp2 amine, diazo, N-heterocyclic ring, pyrimidine or pyridine or with a biphenyl derivative wherein at least one of the ortho, meta or para positions of one or both phenyl rings is independently substituted with a suitable hydrogen bonding functional group selected from —OH, —ROH, —C(O)H, —C(O)R', —COON, —RCOOH, —NH$_2$, —RNH$_2$, —NHR', —RNHR', —NR'$_2$, —RNR'$_2$, —NHOR', —RNHOR' wherein R is an alkylene group or an acyl group (—C(O)R"—), R' is an alkyl group and R" is an alkylene group.

Suitable co-crystal forming compounds containing at least one hydroxyl functional group include, but are not limited to, 1-hydroxy-2-naphthoic acid, 7-oxo-DHEA, acetohydroxamic acid, allopurinaol, ascorbic acid, chrysin, citric acid, D-ribose, galactaric acid, genistein, gentisic acid, N-methyl glucamine, gluconic acid, glucosamine, glucaronic acid, glycolic acid, hydroquinone, lactobionic acid, malic acid, mandelic acid, pamoic acid, pyridoxamine, pyridoxine, quercetin, resveratrol, 4-amino salicylic acid, salicyclic acid, serine, threonine, TRIS, tyrosine, vitamin K5 and xylitol.

Preferred co-crystal forming compounds which have hydroxyl groups are C$_{4-20}$ alkane diols such as 1,9-nonane diol and cyclic polyols such as 2,3,5,6-tetrahydroxybenzoquinone Suitable co-crystal forming compounds containing at least one carboxylic acid functional group include, but are not limited to, 1-hydroxy-2-naphthoic acid, 4-aminobenzoic acid, acetic acid, adipic acid, alanine, arginine, ascorbic acid, asparagine, aspartic acid, benzenesulphonic acid, benzoic acid, 2-phenoxybenzoic acid, 2-acetoxybenzoic acid, camphoric acid, capric acid, cinnamic acid, citric acid, cysteine, dimethylglycine, formic acid, fumaric acid, galactaric acid, gentisic acid, gluconic acid, glucaronic acid, glutamic acid, glutamine, glutaric acid, glycine, glycolic acid, hippuric acid, histidine, isoleucine, lactic acid, lactobionic acid, lauric acid, leucine, lysine, maleic acid, malic acid, malonic acid, mandelic acid, methionine, nicotinic acid, orotic acid, oxalic acid, palmitic acid, pamoic acid, phenylalanine, proline, propionic acid, pyroglutamic acid, pyrazine carboxylic acid, 4-amino salicylic acid, salicyclic acid, sebacic acid, serine, stearic acid, succinic acid, tartaric acid, thiocyanic acid, threonine, trichloroacetic acid, trifluoroacetic acid, tryptophan, tyrosine, valine. Preferred co-crystal forming compounds having carboxylic acid groups are are C$_{4-20}$ alkanoic acids optionally substituted with one to three hydroxyl or amine groups such as 15-hydroxypentadecanoic acid.

Suitable co-crystal forming compounds containing at least one amine functional group include, but are not limited to 4-aminobenzoic acid, 4-aminopyridine, 4-ethoxyphenyl urea, acetohydroxamic acid, adenine, alanine, allopurinaol, arginine, asparagine, aspartic acid, cyclamic acid, cysteine, dimethylglycine, N-methyl glucamine, glutamic acid, glutamine, glycine, hippuric acid, histidine, imidazole, isoleucine, leucine, lysine, methionine, phenylalanine, piperazine, procaine, praline, pyridoxamine, saccharin, serine, threonine, TRIS, tryptophan, tyrosine, urea, valine and vitamin K5. Preferred co-crystal forming compounds having amine groups include methyl hydrazinocarboxylate.

Suitable co-crystal forming compounds containing at least one pyridine group include, but are not limited to, 4-aminopyridine, nicotinamide, nicotinic acid, pyridoxamine and pyridoxine. Preferred co-crystal forming compounds having pyridine groups are pyridines substituted with one or more alkyl groups, hydroxyl groups or amide groups such as 5-hydroxy-2-methyl pyridine, 2-hydroxy-6-methyl pyridine, nicotinamide and isonicotinamide.

Suitable co-crystal forming compounds containing at least one pyrimidine group include 4-(3H)-pyrimidinone.

Preferably, the hydrogen bonding functional group on the biphenyl derivative is selected from one or more of —OH, —ROH, —COON, —RCOOH, —NH$_2$, —RNH$_2$, —NHR' and —RNHR'.

Examples of biphenyl derivatives are 4-aminobiphenyl, 2-aminobiphenyl, 4-phenylbenzylamine, 2-amino-4-phenylphenol, 5-phenyl-o-anisidine, 3,3'-diaminobenzidine, o-dianisidine, biphenyl-4-carboxylic acid, biphenyl-2-carboxylic acid, 4'-methyl-2-biphenylcarboxylic acid, 4-biphenylacetic acid, 4'-hydroxy-4-biphenylcarboxylic acid, fenbufen, 2-phenylphenol, 4-phenylphenol, 3-phenylphenol, 2-biphenylmethanol, biphenyl-4-methanol, 4,4'-dihydroxybiphenyl, 2,2'-biphenol, 2-phenylhydroquinone, 2-methyl-3-biphenylmethanol, 1-(4-biphenylyl)1-ethanol and 2,2'-biphenyldimethanol, N,N,N',N'-tetramethylbenzidine, 2-methyl-3-biphenylmethanol, 1-(4-biphenylyl)1-ethanol, biphenyl-4-carboxaldehyde, 4-acetyl-biphenyl and 4,4'-diacetylbiphenyl.

Most preferably, the biphenyl derivative is 4,4'-dihydroxybiphenyl or 4,4-dihydroxy cyclohexylidine bisphenol.

In the context of the present invention "alkyl" means a linear saturated monovalent hydrocarbon radical of one to six carbon atoms, or a branched saturated monovalent hydrocarbon radical of three to six carbon atoms and "alkylene" means a linear saturated divalent hydrocarbon radical of one to six carbon atoms or a branched saturated divalent hydrocarbon radical or three to six carbon atoms. Suitable alkyl groups are, for example, methyl, ethyl, n-propyl, iso-propyl, n-butyl, sec-butyl, iso-butyl, ter-butyl, n-pentyl, n-hexyl and the like. Suitably alkylene groups are, for example, methylene, ethylene, propylene, 2-methylpropylene and the like.

A preferred group of co-crystal forming compounds comprises 1,9-nonane diol, 2,3,5,6-tetrahydroxybenzoquinone, 15-hydroxypentadecanoic acid, 5-hydroxy-2-methyl pyridine, 2-hydroxy-6-methyl pyridine, nicotinamide, isonicotinamide, 4-(3H)-pyrimidinone, methyl hydrazinocarboxylate, 4,4'-dihydroxybiphenyl, or 4,4-dihydroxy cyclohexylidine bisphenol and of these, particularly preferred are 2,3,5,6-tetrahydroxybenzoquinone, 5-hydroxy-2-methyl pyridine, nicotinamide, isonicotinamide, 4,4'-dihydroxybiphenyl, and 4,4-dihydroxy cyclohexylidine bisphenol The co-crystalline form of propiconazole and the co-crystal forming compound may be characterised by a crystal morphology or by selected peaks of the powder X-ray diffraction pattern expressed in terms of 2 theta angles.

In one embodiment of the invention, there is provided a co-crystal form of propiconazole and 4,4'-dihydroxybiphenyl which is characterised by a powder X-ray diffraction pattern expressed in terms of 2 theta angles, wherein the powder X-ray diffraction pattern comprise the 2 theta angle values listed in Table 1. Table 1 shows the 2 theta values, d spacings, and relative intensity of selected peak positions of the powder X-ray diffraction pattern of a propiconazole-4,4'-dihydroxybiphenyl co-crystal.

TABLE 1

| 2θ (°) | d spacing (Å) | Relative Intensity |
|---|---|---|
| 7.689 | 11.488 | 100.0 |
| 11.513 | 7.680 | 85.8 |
| 16.964 | 5.222 | 60.5 |
| 18.618 | 4.762 | 66.9 |
| 19.178 | 4.624 | 62.3 |

TABLE 1-continued

| 2θ (°) | d spacing (Å) | Relative Intensity |
|---|---|---|
| 21.008 | 4.225 | 60.5 |
| 21.357 | 4.157 | 60.9 |
| 21.923 | 4.051 | 83.2 |
| 22.415 | 3.963 | 69.5 |
| 23.566 | 3.772 | 69.2 |
| 26.254 | 3.392 | 66.5 |
| 26.958 | 3.305 | 63.6 |

It has surprisingly been found that when propiconazole and a co-crystal forming compound are allowed to form co-crystals, the resulting co-crystals give rise to improved properties of the propiconazole as compared to propiconazole in free form. In particular, the co-crystals exhibit substantially higher melting points than the propiconazole alone: for example, differential scanning calorimetry results for propiconazole and 4,4'-dihydroxybiphenyl co-crystals showed that the co-crystals exhibit a single melting endotherm at a temperature of between 126-130° C., substantially higher than that observed for propiconazole alone. This increased melting point is important as it has benefits during manufacturing, formulation and storage. In particular, this new solid state of propiconazole, which has a melting point above the temperature range normally associated with processing and storage, will not undergo melting and recrystallisation events during its formulation and nor will it undergo recrystallisation events during storage of both the technical grade material and the formulated material—the technical material and the formulation will therefore retain their homogeneity. In addition, the higher melting point will allow new solid formulation formats, such as suspension concentrates, suspo-emulsions and wet granulations, to be developed and will lead to potential purity benefits (due to the ability to isolate the solid state rather than a liquid) as well as improved handling characteristics (e.g. reduced toxicity). Finally, mixtures of this new solid state of propiconazole with other active ingredients should show improved stability as potential depression of the melting point by the other active ingredients will not be as crucial.

As used herein 'co-crystal' means a crystalline material which comprises two or more unique components in a stoichiometric ratio each containing distinctive physical characteristics such as structure, melting point and heat of fusion. The co-crystal can be constructed through several modes of molecular recognition including hydrogen-bonding, II (pi)-stacking, guest-host complexation and Van-Der-Waals interactions. Of the interactions listed above, hydrogen-bonding is the dominant interaction in the formation of the co-crystal, whereby a non-covalent bond is formed between a hydrogen bond donor of one of the moieties and a hydrogen bond acceptor of the other. Preferred co-crystals of the present invention are those where hydrogen bonding occurs between the co-crystal forming compound and the propiconazole.

It is noted that hydrogen bonding can result in several different intermolecular assemblies and, as such, the co-crystals of the present invention may exist in one or more polymeric forms. A polymorphic co-crystal may contain any ratio of active ingredient to co-former, but typically will be in the range of 3:1 to 1:3. As the propiconazole exhibits isomerism, a polymorphic form may also contain a different isomeric ratio. This will also be the case when the co-crystal forming compound exhibits isomerism. Each polymorphic form can be defined by one or more solid state analytical techniques including single crystal X-ray diffraction, powder X-ray diffraction, DSC, Raman or Infra-red spectroscopy.

As used herein, the term 'propiconazole' refers to (±)-1-[2-(2,4-dichlorophenyl)-4-propyl-1,3-dioxolan-2-ylmethyl]-1H-1,2,4-triazole, its four sterioisomers (2R, 4S; 2S, 4R; 2R, 4R; 2S, 4S), diastereomeric pairs thereof and mixtures of the diastereomeric pairs. In particular, 'propiconazole' refers to commercially available propiconazole technical material.

Suitably, the ratio of propiconazole to co-crystal forming compounds in the co-crystal is in the range of from 3:1 to 1:3. More suitably, the ratio of propiconazole to co-crystal forming compounds in the co-crystal is in the range of from 2:1 to 1:1. Most suitably, the ratio of propiconazole to co-crystal forming compound in the co-crystal is approximately 2:1.

The co-crystals of the present invention are formed by contacting the propiconazole with a co-crystal forming compound. This may be done by (i) grinding two solids together, (ii) melting one or both components and allowing them to recrystallise, (iii) solubilising the propiconazole and adding the co-crystal forming compound or (iv) solubilising the co-crystal forming compound and adding the propiconazole. It may also be possible to solubilise the propiconazole in the co-crystal forming compound and vice versa. Crystallisation is then allowed to occur under suitable conditions. For example, crystallisation may require alteration of a property of the solutions, such as pH or temperature and may require concentration of solute, usually by removal of the solvent and typically by drying the solution. Solvent removal results in the concentration of propiconazole increasing over time so as to facilitate crystallisation. Once the solid phase comprising any crystals is formed, this may be tested as described herein.

Accordingly, the present invention provides a process for the production of a co-crystal of propiconazole and a co-crystal forming compound comprising (a) grinding, heating or contacting in solution propiconazole with the co-crystal forming compound, under crystallisation conditions so as to form a solid phase;

(b) isolating co-crystals comprising propiconazole and the co-crystal forming compound.

The co-crystal forming compound for use in the process of the invention is as defined above. In one embodiment of the process, the biphenyl derivative is 1,9-nonane diol, 2,3,5,6-tetrahydroxybenzoquinone, 15-hydroxypentadecanoic acid, 5-hydroxy-2-methyl pyridine, 2-hydroxy-2-methyl pyridine, nicotinamide, isonicotinamide, 4-(3H)-pyrimidinone, methyl hydrazinocarboxylate, 4,4'-dihydroxybiphenyl, or 4,4-dihydroxy cyclohexylidine bisphenol.

Assaying the solid phase for the presence of co-crystals of propiconazole and the co-crystal forming compound may be carried out by conventional methods known in the art. For example, it is convenient and routine to use powder X-ray diffraction techniques to assess the presence of the co-crystals. This may be effected by comparing the spectra of the propiconazole, co-crystal forming compound and putative co-crystals in order to establish whether or not true co-crystals have been formed. Other techniques used in an analogous fashion, include differential scanning calorimetry (DSC), thermogravimetric analysis (TGA) and Raman spectroscopy. Single crystal X-ray diffraction is especially useful in identifying co-crystal structures.

The co-crystals of the invention may be readily incorporated into fungicidal compositions (including agrochemical compositions and compositions for use in the protection of industrial materials) by conventional means. Accordingly, the invention also provides a fungicidal composition comprising a co-crystal of propiconazole and the co-crystal forming compound, wherein the co-crystal forming compound is as defined above. In a further embodiment, the fungicidal composition is an agrochemical composition.

The agrochemical compositions comprising the co-crystals of the present invention can be used for the control of plant pathogenic fungi on a number of plant species. Accordingly, the invention also provides a method of preventing/controlling fungal infection on plants or plant propagation material comprising treating the plant or plant propagation material with a fungicidally effective amount of an agricultural composition of the invention. By 'plant propagation material' is meant seeds of all kinds (fruit, tubers, bulbs, grains etc), cuttings, cut shoots and the like.

In particular, the agrochemical compositions of the invention can be used to control, for example, *Cochliobolus sativus, Erysiphe graminis, Leptosphaeria nodorum, Puccinia* spp., *Pyrenophora teres, Pyrenophora tritici-repentis, Rhynchosporium secalis, Septoria* spp, *Mycosphaerella musicola, Mycosphaerella fijiensis* var. *difformis, Sclerotinia homoeocarpa, Rhizoctonia solani, Puccinia* spp., *Erysiphe gramini, Rhizoctonia solani, Helminthosporium oryzae,* dirty panicle complex, *Hemileia vastatrix, Cercospora* spp., *Monilinia* spp., *Podosphaera* spp., *Sphaerotheca* spp., *Tranzschelia* spp. and *Helminthosporium* spp.

The agrochemical compositions of the present invention are suitable for controlling such disease on a number of plants and their propagation material including, but not limited to the following target crops: cereals (wheat, barley, rye, oats, maize (including field corn, pop corn and sweet corn), rice, sorghum and related crops); beet (sugar beet and fodder beet); leguminous plants (beans, lentils, peas, soybeans); oil plants (rape, mustard, sunflowers); cucumber plants (marrows, cucumbers, melons); fibre plants (cotton, flax, hemp, jute); vegetables (spinach, lettuce, asparagus, cabbages, carrots, eggplants, onions, pepper, tomatoes, potatoes, paprika, okra); plantation crops (bananas, fruit trees, rubber trees, tree nurseries), ornamentals (flowers, shrubs, broad-leaved trees and evergreens, such as conifers); as well as other plants such as vines, bushberries (such as blueberries), caneberries, cranberries, peppermint, rhubarb, spearmint, sugar cane and turf grasses including, but not limited to, cool-season turf grasses (for example, bluegrasses (*Poa* L.), such as Kentucky bluegrass (*Poa pratensis* L.), rough bluegrass (*Poa trivialis* L.), Canada bluegrass (*Poa compressa* L.) and annual bluegrass (*Poa annua* L.); bentgrasses (*Agrostis* L.), such as creeping bentgrass (*Agrostis palustris* Huds.), colonial bentgrass (*Agrostis tenius* Sibth.), velvet bentgrass (*Agrostis canina* L.) and redtop (*Agrostis alba* L.); fescues (*Festuca* L.), such as tall fescue (*Festuca arundinacea* Schreb.), meadow fescue (*Festuca elatior* L.) and fine fescues such as creeping red fescue (*Festuca rubra* L.), chewings fescue (*Festuca rubra* var. commutata Gaud.), sheep fescue (*Festuca ovina* L.) and hard fescue (*Festuca longifolia*); and ryegrasses (*Lolium* L.), such as perennial ryegrass (*Lolium perenne* L.) and annual (Italian) ryegrass (*Lolium multiflorum* Lam.)) and warm-season turf grasses (for example, Bermudagrasses (*Cynodon* L. C. Rich), including hybrid and common Bermudagrass; Zoysiagrasses (*Zoysia Willd*.), St. Augustinegrass (*Stenotaphrum secundatum* (Walt.) Kuntze); and centipedegrass (*Eremochloa ophiuroides* (Munro.) Hack.)).

In addition 'crops' are to be understood to include those crops that have been made tolerant to pests and pesticides, including herbicides or classes of herbicides, as a result of conventional methods of breeding or genetic engineering. Tolerance to e.g. herbicides means a reduced susceptibility to damage caused by a particular herbicide compared to conventional crop breeds. Crops can be modified or bred so as to be tolerant, for example, to HPPD inhibitors such as mesotrione or EPSPS inhibitors such as glyphosate.

The rate at which the agrochemical composition of the invention is applied will depend upon the particular type of fungus to be controlled, the degree of control required and the timing and method of application. In general, the compositions of the invention can be applied at an application rate of between 0.005 kilograms/hectare (kg/ha) and about 5.0 kg/ha, based on the total amount of active propiconazole in the composition. An application rate of between about 0.1 kg/ha and about 3.0 kg/ha is preferred, with an application rate of between about 0.2 kg/ha and 1 kg/ha being especially preferred.

In practice, the agrochemical compositions comprising the co-crystals of the invention are applied as a formulation containing the various adjuvants and carriers known to or used in the industry. They may thus be formulated as granules, as wettable powders, as emulsifiable concentrates, as suspension concentrates, as powders or dusts, as flowables, as solutions, as suspensions or emulsions or suspo-emulsions, or as controlled release forms such as microcapsules. Suitably, the agrochemical composition of the invention may be formulated as a suspension concentrate, a suspo-emulsion or a wet granulation. These formulations are described in more detail below and may contain as little as about 0.5% to as much as about 95% or more by weight of the active ingredient in the form of the co-crystal. The optimum amount will depend on formulation, application equipment and nature of the plant pathogenic fungi to be controlled.

Wettable powders are in the form of finely divided particles which disperse readily in water or other liquid carriers. The particles contain the active ingredient retained in a solid matrix. Typical solid matrices include fuller's earth, kaolin clays, silicas and other readily wet organic or inorganic solids. Wettable powders normally contain about 5% to about 95% of the active ingredient plus a small amount of wetting, dispersing or emulsifying agent.

Emulsifiable concentrates are homogeneous liquid compositions dispersible in water or other liquid and may consist entirely of the active compound with a liquid or solid emulsifying agent, or may also contain a liquid carrier, such as xylene, heavy aromatic naphthas, isophorone and other non-volatile organic solvents. In use, these concentrates are dispersed in water or other liquid and normally applied as a spray to the area to be treated. The amount of active ingredient may range from about 0.5% to about 95% of the concentrate.

Suspension concentrates are aqueous formulations in which finely divided solid particles of the active compound are stably suspended. Such formulations include anti-settling agents and dispersing agents and may further include a wetting agent to enhance activity as well an anti-foam and a crystal growth inhibitor. In use, these concentrates are diluted in water and normally applied as a spray to the area to be treated. The amount of active ingredient may range from about 0.5% to about 95% of the concentrate.

Granular formulations include both extrudates and relatively coarse particles and are usually applied without dilution to the area in which control of plant pathogenic fungi is required. Typical carriers for granular formulations include sand, fuller's earth, attapulgite clay, bentonite clays, montmorillonite clay, vermiculite, perlite, calcium carbonate, brick, pumice, pyrophyllite, kaolin, dolomite, plaster, wood flour, ground corn cobs, ground peanut hulls, sugars, sodium chloride, sodium sulphate, sodium silicate, sodium borate, magnesia, mica, iron oxide, zinc oxide, titanium oxide, antimony oxide, cryolite, gypsum, diatomaceous earth, calcium sulphate and other organic or inorganic materials which absorb or which can be coated with the active compound. Granular formulations normally contain about 5% to about 25% active ingredients which may include surface-active agents such as heavy aromatic naphthas, kerosene and other petroleum fractions, or vegetable oils; and/or stickers such as dextrins, glue or synthetic resins.

Dusts are free-flowing admixtures of the active ingredient with finely divided solids such as talc, clays, flours and other organic and inorganic solids which act as dispersants and carriers.

Microcapsules are typically droplets or granules of the active ingredient enclosed in an inert porous shell which allows escape of the enclosed material to the surroundings at controlled rates. Encapsulated droplets are typically about 1 to 50 microns in diameter. The enclosed liquid typically constitutes about 50 to 95% of the weight of the capsule and may include solvent in addition to the active compound. Encapsulated granules are generally porous granules with porous membranes sealing the granule pore openings, retaining the active species in liquid form inside the granule pores. Granules typically range from 1 millimetre to 1 centimetre and preferably 1 to 2 millimetres in diameter. Granules are formed by extrusion, agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for agrochemical applications include simple solutions of the active ingredient in a solvent in which it is completely soluble at the desired concentration, such as acetone, alkylated naphthalenes, xylene and other organic solvents. Pressurised sprayers, wherein the active ingredient is dispersed in finely-divided form as a result of vaporisation of a low boiling dispersant solvent carrier, may also be used.

Many of the formulations described above include wetting, dispersing or emulsifying agents. Examples are alkyl and alkylaryl sulphonates and sulphates and their salts, polyhydric alcohols; polyethoxylated alcohols, esters and fatty amines These agents, when used, normally comprise from 0.1% to 15% by weight of the formulation.

Suitable agricultural adjuvants and carriers that are useful in formulating the compositions of the invention in the formulation types described above are well known to those skilled in the art. Suitable examples of the different classes are found in the non-limiting list below.

Liquid carriers that can be employed include water, toluene, xylene, petroleum naphtha, crop oil, acetone, methyl ethyl ketone, cyclohexanone, acetic anhydride, acetonitrile, acetophenone, amyl acetate, 2-butanone, chlorobenzene, cyclohexane, cyclohexanol, alkyl acetates, diacetonalcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethyl formamide, dimethyl sulfoxide, 1,4-dioxane, dipropylene glycol, dipropylene glycol methyl ether, dipropylene glycol dibenzoate, diproxitol, alkyl pyrrolidinone, ethyl acetate, 2-ethyl hexanol, ethylene carbonate, 1,1,1-trichloroethane, 2-heptanone, alpha pinene, d-limonene, ethylene glycol, ethylene glycol butyl ether, ethylene glycol methyl ether, gamma-butyrolactone, glycerol, glycerol diacetate, glycerol monoacetate, glycerol triacetate, hexadecane, hexylene glycol, isoamyl acetate, isobomyl acetate, isooctane, isophorone, isopropyl benzene, isopropyl myristate, lactic acid, laurylamine, mesityl oxide, methoxy-propanol, methyl isoamyl ketone, methyl isobutyl ketone, methyl laurate, methyl octanoate, methyl oleate, methylene chloride, m-xylene, n-hexane, n-octylamine, octadecanoic acid, octyl amine acetate, oleic acid, oleylamine, o-xylene, phenol, polyethylene glycol (PEG400), propionic acid, propylene glycol, propylene glycol monomethyl ether, p-xylene, toluene, triethyl phosphate, triethylene glycol, xylene sulfonic acid, paraffin, mineral oil, trichloroethylene, perchloroethylene, ethyl acetate, amyl acetate, butyl acetate, methanol, ethanol, isopropanol, and higher molecular weight alcohols such as amyl alcohol, tetrahydrofurfuryl alcohol, hexanol, octanol, etc. ethylene glycol, propylene glycol, glycerine, N-methyl-2-pyrrolidinone, and the like. Water is generally the carrier of choice for the dilution of concentrates.

Suitable solid carriers include talc, titanium dioxide, pyrophyllite clay, silica, attapulgite clay, kieselguhr, chalk, diatomaceous earth, lime, calcium carbonate, bentonite clay, fuller's earth, cotton seed hulls, wheat flour, soybean flour, pumice, wood flour, walnut shell flour, lignin and the like.

A broad range of surface-active agents are advantageously employed in both said liquid and solid compositions, especially those designed to be diluted with carrier before application. The surface-active agents can be anionic, cationic, non-ionic or polymeric in character and can be employed as emulsifying agents, wetting agents, suspending agents or for other purposes. Typical surface active agents include salts of alkyl sulphates, such as diethanolammonium lauryl sulphate; alkylarylsulphonate salts, such as calcium dodecylbenzenesulphonate; alkylphenol-alkylene oxide addition products, such as nonylphenol-C.sub. 18 ethoxylate; alcohol-alkylene oxide addition products, such as tridecyl alcohol-C.sub. 16 ethoxylate; soaps, such as sodium stearate; alkylnaphthalenesulphonate salts, such as sodium dibutylnaphthalenesulphonate; dialkyl esters of sulphosuccinate salts, such as sodium di(2-ethylhexyl)sulphosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly utilized in agricultural compositions include crystallisation inhibitors, viscosity modifiers, suspending agents, spray droplet modifiers, pigments, antioxidants, foaming agents, light-blocking agents, compatibilizing agents, antifoam agents, sequestering agents, neutralising agents and buffers, corrosion inhibitors, dyes, odorants, spreading agents, penetration aids, micronutrients, emollients, lubricants, sticking agents, and the like.

In addition, further, other biocidally active ingredients or compositions may be combined with the agrochemical composition of this invention. For example, the compositions may contain other fungicides, herbicides, insecticides, bactericides, acaricides, nematicides and/or plant growth regulators, in order to broaden the spectrum of activity or in order to reduce the risk of resistance developing.

Each of the above formulations can be prepared as a package containing the fungicides together with other ingredients of the formulation (diluents, emulsifiers, surfactants, etc.). The formulations can also be prepared by a tank mix method, in which the ingredients are obtained separately and combined at the grower site.

These formulations can be applied to the areas where control is desired by conventional methods. Dust and liquid compositions, for example, can be applied by the use of power-dusters, broom and hand sprayers and spray dusters. The formulations can also be applied from airplanes as a dust or a spray or by rope wick applications. Both solid and liquid formulations may also be applied to the soil in the locus of the plant to be treated allowing the active ingredient to penetrate the plant through the roots. The formulations of the invention may also be used for dressing applications on plant propagation material to provide protection against fungus infections on the plant propagation material as well as against phytopathogenic fungi occurring in the soil. Suitably, the active ingredient may be applied to plant propagation material to be protected by impregnating the plant propagation material, in particular, seeds, either with a liquid formulation of the fungicide or coating it with a solid formulation. In special cases, other types of application are also possible, for example, the specific treatment of plant cuttings or twigs serving propagation.

Suitably, the agrochemical compositions and formulations of the present invention are applied prior to disease development. Rates and frequency of use of the formulations are those conventionally used in the art and will depend on the risk of infestation by the fungal pathogen.

The compositions of the invention can also be used for the protection of industrial materials. In a still further aspect of the invention there is thus provided a method for the protection of industrial material from fungal attack comprising treating the industrial material with a composition comprising the co-crystal of the invention. In a further aspect, the present invention provides the use of a composition which comprises the co-crystal of the invention for the protection of industrial materials. In a particular embodiment said industrial material is selected from the group consisting of: wood; plastic; wood plastic composite; paint; paper; and wallboards.

"Industrial material" includes, but is not limited to, those materials used in construction and the like. For example, industrial material may be structural timber, doors, cupboards, storage units, carpets, particularly natural fibre carpets such as wool and hessian, plastics, wood (including engineered wood) and wood plastic composite.

In a particular embodiment the industrial material is a coating. "Coating" includes, but is not limited to, compositions applied to a substrate, for example, paints, stains, varnishes, lacquers, primers, semi gloss coatings, gloss coatings, flat coatings, topcoats, stain-blocking coatings, penetrating sealers for porous substrates, concrete, and marble, elastomeric coatings, mastics, caulks, and sealants, board and panelling coatings, transportation coatings, furniture coatings, and coil coatings, bridge and tank coatings and surface marking paints, leather coatings and treatments, floor care coatings, paper coatings, personal care coatings such as for hair, skin, nails, woven and nonwoven fabric coatings and pigment printing pastes, and adhesive coatings such as, for example, pressure sensitive adhesives and wet- and dry-laminating adhesives and plaster.

In particular embodiment coating means paint; varnish; stain, lacquer or plaster. In a further embodiment said coating is a lacquer. In a specific embodiment coating means paint. Paint can comprise, for example, a film former and a carrier (which carrier can be water and/or an organic solvent) and optionally a pigment.

In addition to this, industrial material includes adhesives, sealants, joining materials and joints and insulation material. In a particular embodiment "industrial material" means structural timber. In a further embodiment "industrial material" means engineered wood. In a further embodiment "industrial material" means plastic.

Plastics includes plastic polymers and copolymers, including: acrylonitrile butadiene styrene, butyl rubber, epoxies, fluoropolymers, isoprene, nylons, polyethylene, polyurethane, polypropylene, polyvinyl chloride, polystyrene, polycarbonate, polyvinylidene fluoride, polyacrylate, polymethyl methacrylate, polyurethane, polybutylene, polybutylene terephthalate, polyether sulphone, polyphenyllenoxide, polyphenylene ether, polyphenylene sulphide, polyphtatamide, polysulphene, polyester, silicone, styrene butadiene rubber and combinations of polymers. In a further embodiment "industrial material" means polyvinyl chloride (PVC). In a further embodiment "industrial material" means polyurethane (PU). In a further embodiment "industrial material" means wood plastic composite (WPC). Wood plastic composite is a material that is well known in the art. A review of WPCs can be found in the following publication-Craig Clemons-Forrest Products Journal. June 2002 Vol 52. No. 6. pp 10-18.

"Wood" is to be understood as meaning wood and wood products, for example: derived timber products, lumber, plywood, chipboard, flakeboard, laminated beams, oriented strandboard, hardboard, and particleboard, tropical wood, structural timber, wooden beams, railway sleepers, components of bridges, jetties, vehicles made of wood, boxes, pallets, containers, telegraph-poles, wooden fences, wooden lagging, windows and doors made of wood, plywood, chipboard, joinery, or wooden products which are used, quite generally, for building houses or decks, in building joinery or wood products that are generally used in house-building including engineered wood, construction and carpentry.

"Industrial material" also includes cooling lubricants and cooling and heating systems, ventilation and air conditioning systems and parts of production plants, for example cooling-water circuits.

"Industrial material" also includes wallboards such as gypsum based wallboards.

In a still further aspect of the invention there is provided an industrial material comprising a composition which comprises a co-crystal of the invention. In a particular embodiment said industrial materials are selected from the group consisting of wood, plastic, wood plastic composite, paint, paper and wallboards. In a particular embodiment said industrial materials comprise wood.

The industrial material can be treated with a composition according to the invention in a number of ways, including, but not limited to, by including the composition in the industrial material itself, absorbing, impregnating, treating (in closed pressure or vacuum systems) said material with said composition, dipping or soaking the building material, or coating the building material for example by curtain coating, roller, brush, spray, atomisation, dusting, scattering or pouring application. The composition of the invention can be formulated for use in treatment of industrial materials by using techniques well known to the person skilled in the art. Such formulations may utilise, for example, the formulation materials listed above in relation to agrochemical formulations.

The present invention will now be described by way of the following non-limiting examples and figures.

EXAMPLES

1. Preparation of propiconazole/4,4'-dihydroxybiphenyl co-crystals

A 2 litre round bottom flask was set up with overhead stirrer, thermometer, charging funnel and condenser. 405.5 g of propiconazole (technical grade) was charged, with 400 ml of ethanol. The propiconazole solution was agitated for 30 minutes at 40° C. until solubilised. 111.76 g of 4,4'-dihydroxybiphenyl was then added. The reaction mixture was heated to 40° C. Upon heating the 4,4'-dihydroxybiphenyl dissolves to form a clear solution and crystallisation ensues with the formation of a white precipitate. The reaction mixture was agitated for 1 hour at 40° C. and subsequently cooled to 5° C. The solids were isolated by filtration on Buchner apparatus and allowed to dry in air.

FIG. 1 shows the powder X-Ray diffraction patterns of (a) propiconazole technical grade, (b) propiconazole-4,4'-dihydroxybiphenyl co-crystal and (c) 4,4'-dihydroxybiphenyl.

Figure 2:
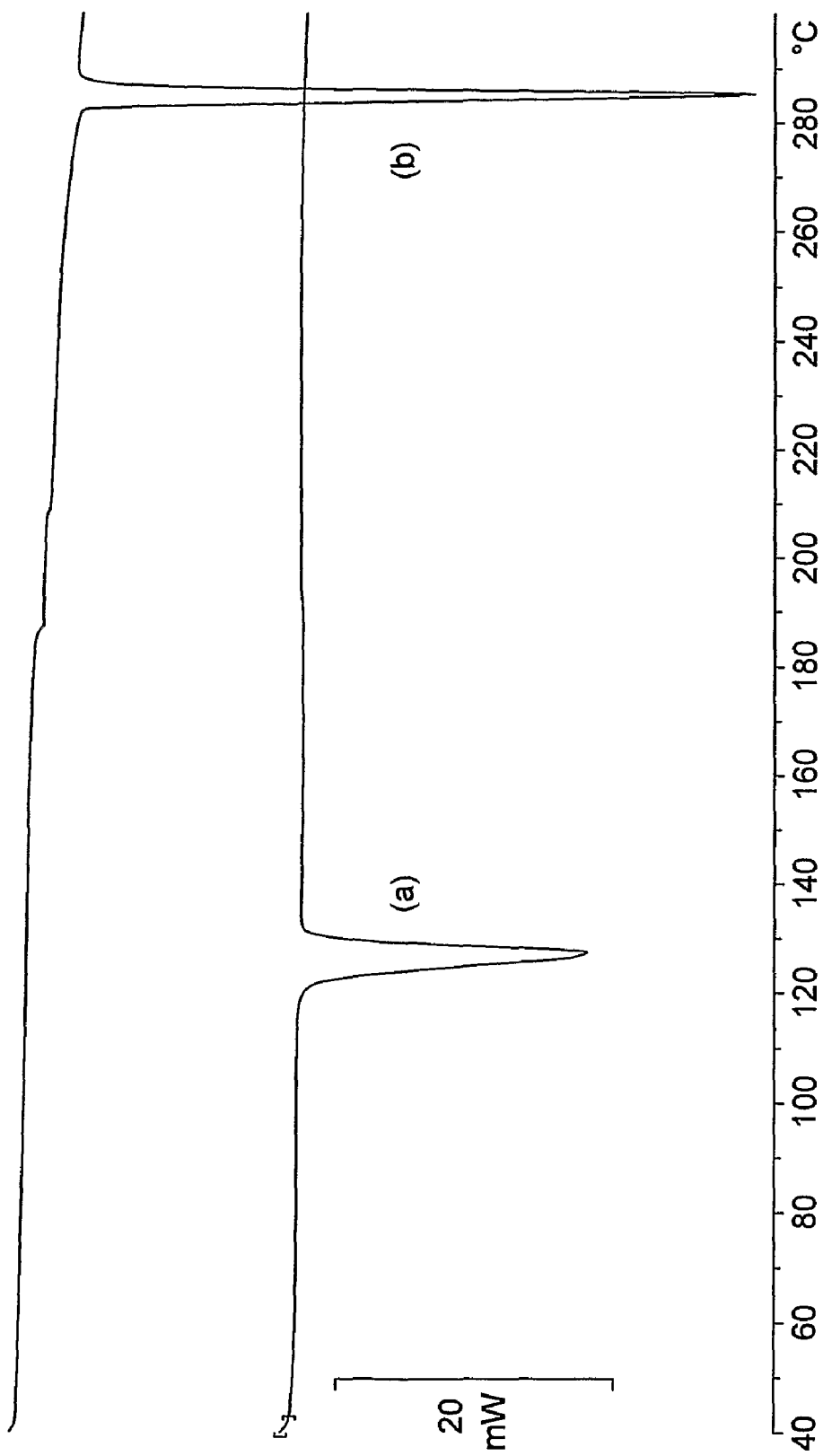
FIG. 2 shows the Differential Scanning calorimetry (DSC) traces of (a) propiconazole-4,4'-dihydroxybiphenyl co-crystal and (b) 4,4'-dihydroxybiphenyl.

FIG. 2—shows Differential Scanning Calorimetry traces of (a) propiconazole-4,4'-dihydroxybiphenyl co-crystal and (b) 4,4'-dihydroxybiphenyl.

Figure 3:
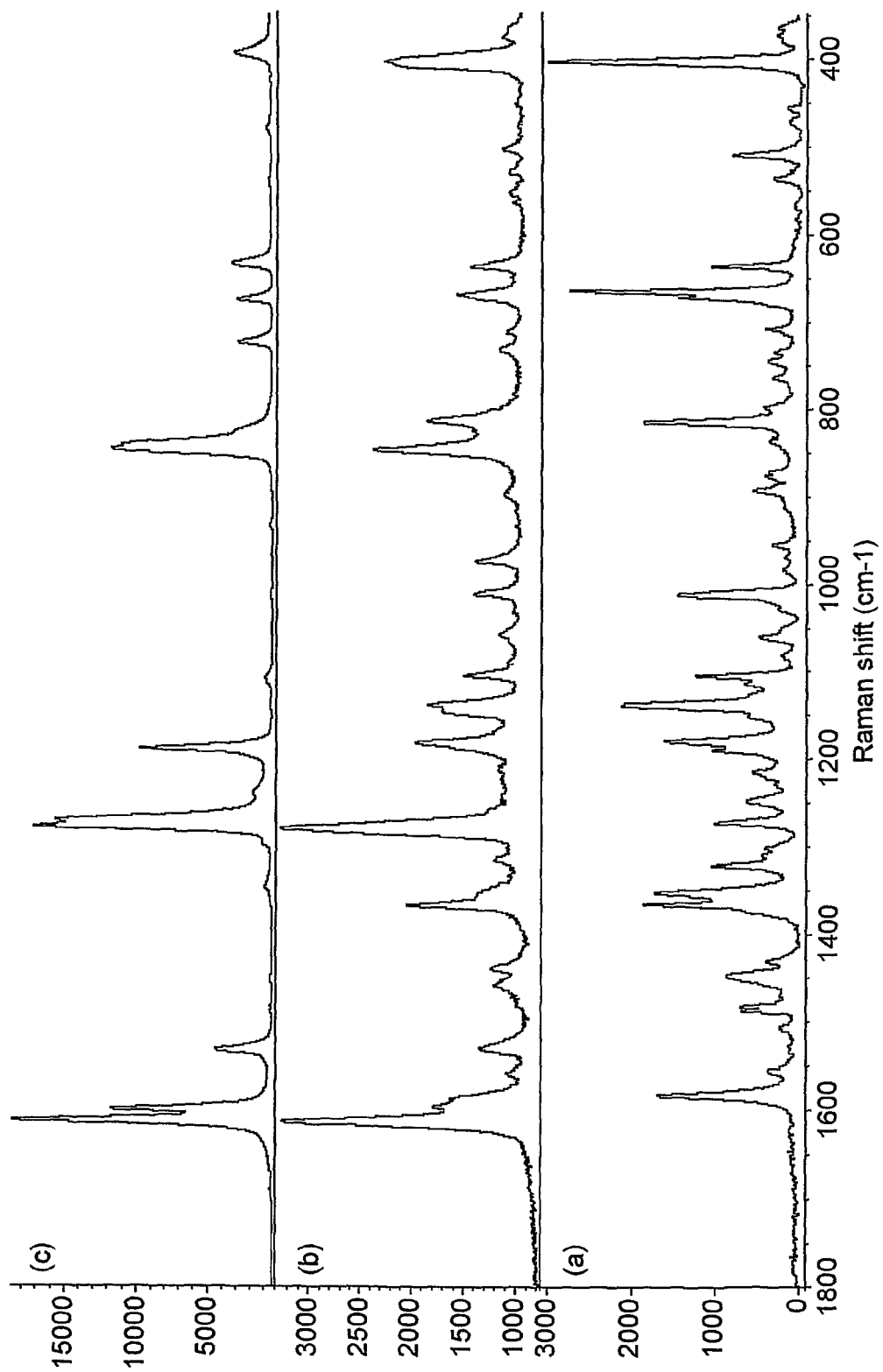
FIG. 3 shows the Raman spectra of (a) propiconazole technical grade, (b) propiconazole-4,4'-dihydroxybiphenyl co-crystal and (c) 4,4'-dihydroxybiphenyl.

FIG. 3—shows Raman spectra of (a) propiconazole technical grade, (b) propiconazole-4,4'-dihydroxybiphenyl co-crystal and (c) 4,4'-dihydroxybiphenyl.

Powder X-ray diffraction analysis clearly shows that the product bears no resemblance to either of its constituent phases suggesting that a new solid state has been formed.

A differential scanning calorimetry trace of the product exhibits a single melting endotherm at 130° C. The constituent phases melt at 61° C. for propiconazole technical grade and 292° C. for 4,4'-dihydroxybiphenyl.

Stability of propiconazole/4,4'-dihydroxybiphenyl co-crystals

The following suspension concentrate of the propiconazole/4,4'-dihydroxybiphenyl co-crystal was prepared:

TABLE 2

|  | % w/v |
| --- | --- |
| Co-crystal | 38.6 |
| Morwet D425 | 3.86 |
| Atlox 4913 | 1.2 |
| Kelzan ASX | 0.3 |
| Proxel GXL | 0.2 |
| Water | rest |

The formulation was assessed after 2 weeks, 1 month and 3 months in various accelerated storage programmes. In all cases, minimal changes were seen in pH, viscosity, particle size and dispersion and suspension characteristics suggesting that the formulations were physically stable.

Biological activity of propiconazole/4,4'-dihydroxybiphenyl co-crystals

The activity of the formulation above was assessed against *Leptosphaeria* spp., *Puccinia* spp., *Rhynchosporium* spp. and *Septoria* spp. under glasshouse and field conditions in comparison with commercially available formulations of propiconazole. Activity of the co-crystal against all fungal species was very similar to the commercially available forms of propiconazole.

2. Propiconazole-4,4-Cyclohexylidene bisphenol co-crystal

Figure 4:
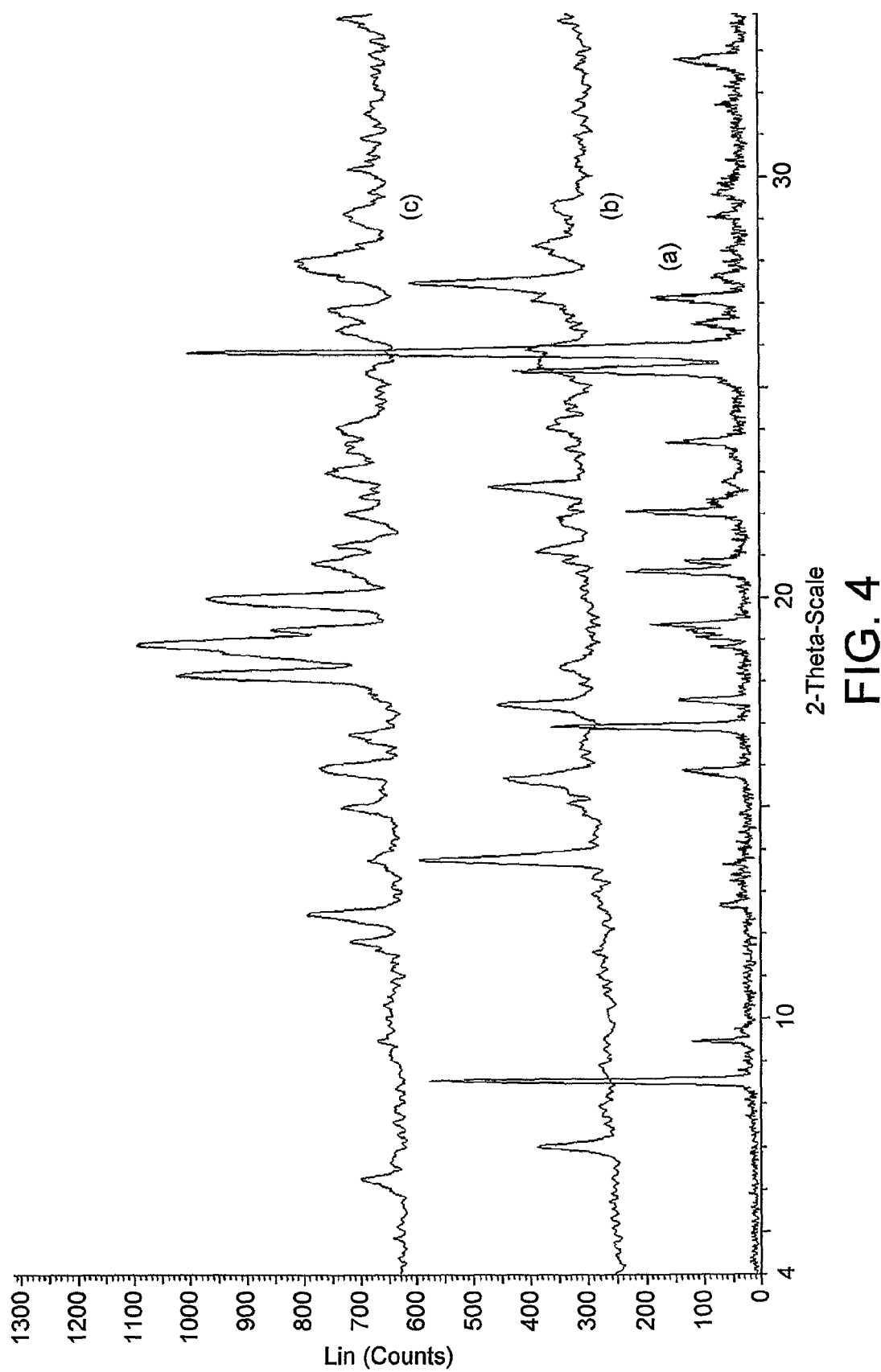
FIG. 4 shows the Powder X-Ray Diffraction patterns of Propiconazole (a), Propiconazole-4,4-Cyclohexylidene bisphenol co-crystal (b) and 4,4-Cyclohexylidene bisphenol (c)

FIG. 4: Powder X-Ray Diffraction patterns of Propiconazole (a), Propiconazole-4,4-Cyclohexylidene bisphenol Co-Crystal (b) and 4,4-Cyclohexylidene bisphenol (c).

Figure 5:
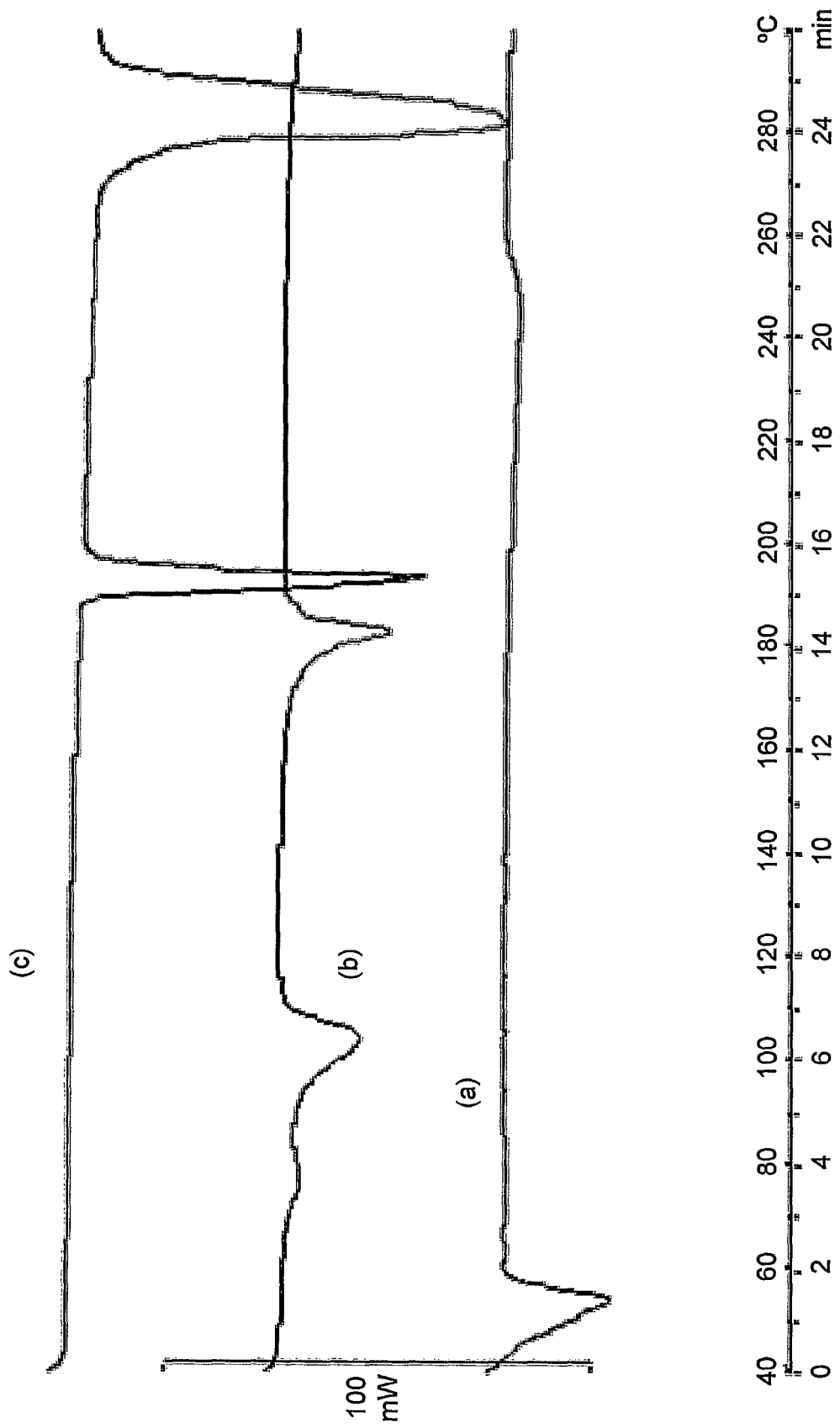
FIG. 5 shows the DSC traces of Propiconazole (a), Propiconazole-4,4-Cyclohexylidene bisphenol co-crystal (b) and 4,4-Cyclohexylidene bisphenol (c)

FIG. 5: DSC traces of Propiconazole (a), Propiconazole-4,4-Cyclohexylidene bisphenol Co-Crystal (b) and 4,4-Cyclohexylidene bisphenol (c).

Table 3: 2θ values of selected peak positions of the Powder X-Ray Diffraction patterns of Propiconazole 4,4-Cyclohexylidene bisphenol Co-Crystal.

TABLE 3

| PPZ - 4,4-Cyclohexylidene bisphenol Co-Crystal 2θ |
| --- |
| 6.968 |
| 13.783 |
| 15.073 |
| 15.656 |
| 17.437 |
| 18.357 |
| 21.120 |
| 21.857 |
| 22.686 |
| 24.159 |
| 25.541 |
| 26.001 |
| 27.045 |
| 27.536 |
| 28.426 |
| 29.347 |

Experimental

For a 1:2 Co-Crystal by Evaporative Crystallisation.

2 g of PPZ was added to a 40 ml vial with 5 ml Isohexane.

3.14 g of 4,4-Cyclohexylidene bisphenol in 5 ml Ethanol was added to this mixture.

The sample was kept at 50° C. for 2 hours and then allowed to cool, and evaporate, before being filtered on a Buchner.

3 Propiconazole-Isonicotinamide co-crystal

Figure 6:
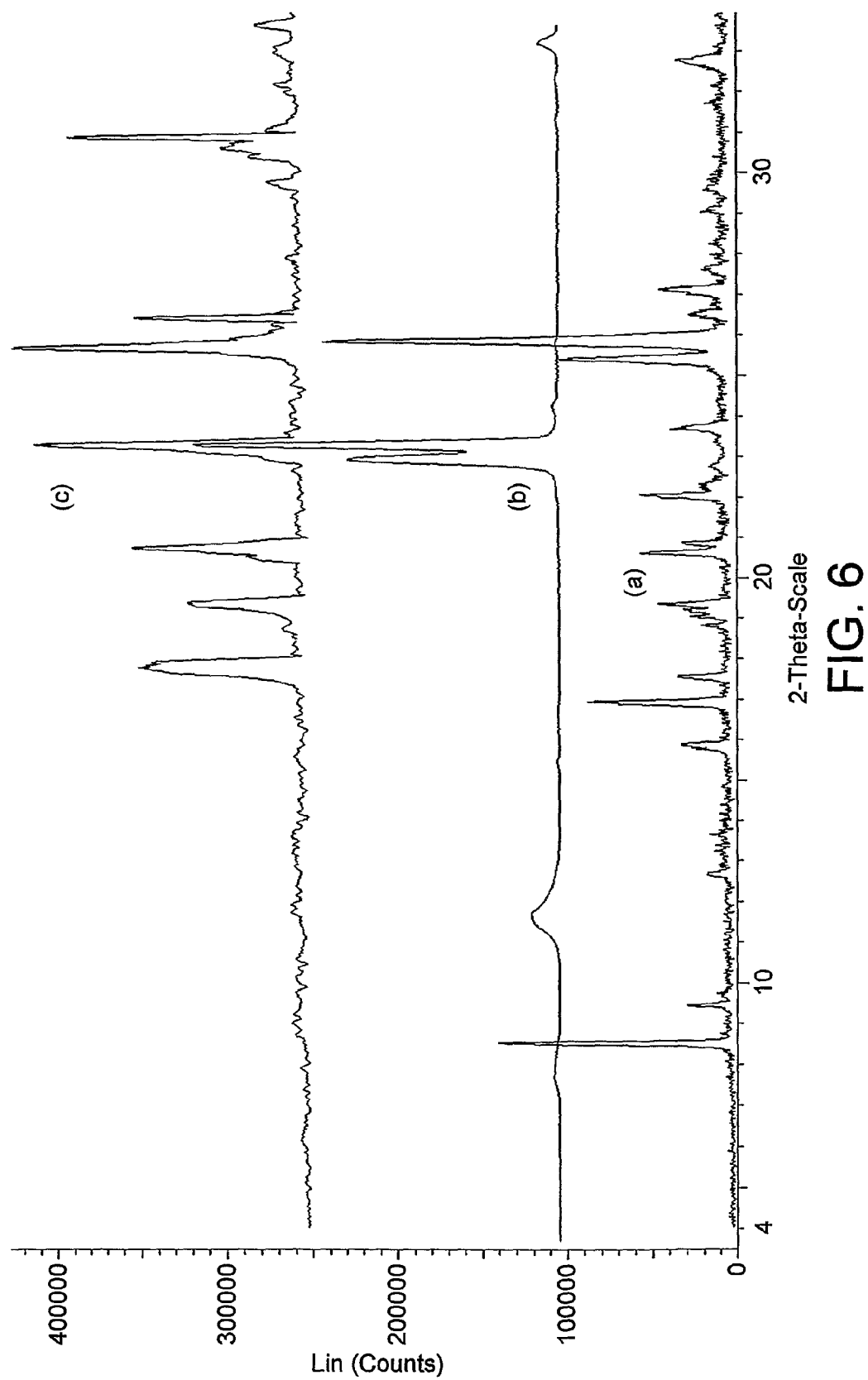
FIG. 6 shows the Powder X-Ray Diffraction patterns of Propiconazole (a), Propiconazole-Isonicotinamide co-crystal (b) and Isonicotinamide (c)

FIG. 6: Powder X-Ray Diffraction patterns of Propiconazole (a), Propiconazole-Isonicotinamide Co-Crystal (b) and Isonicotinamide (c).

Figure 7:
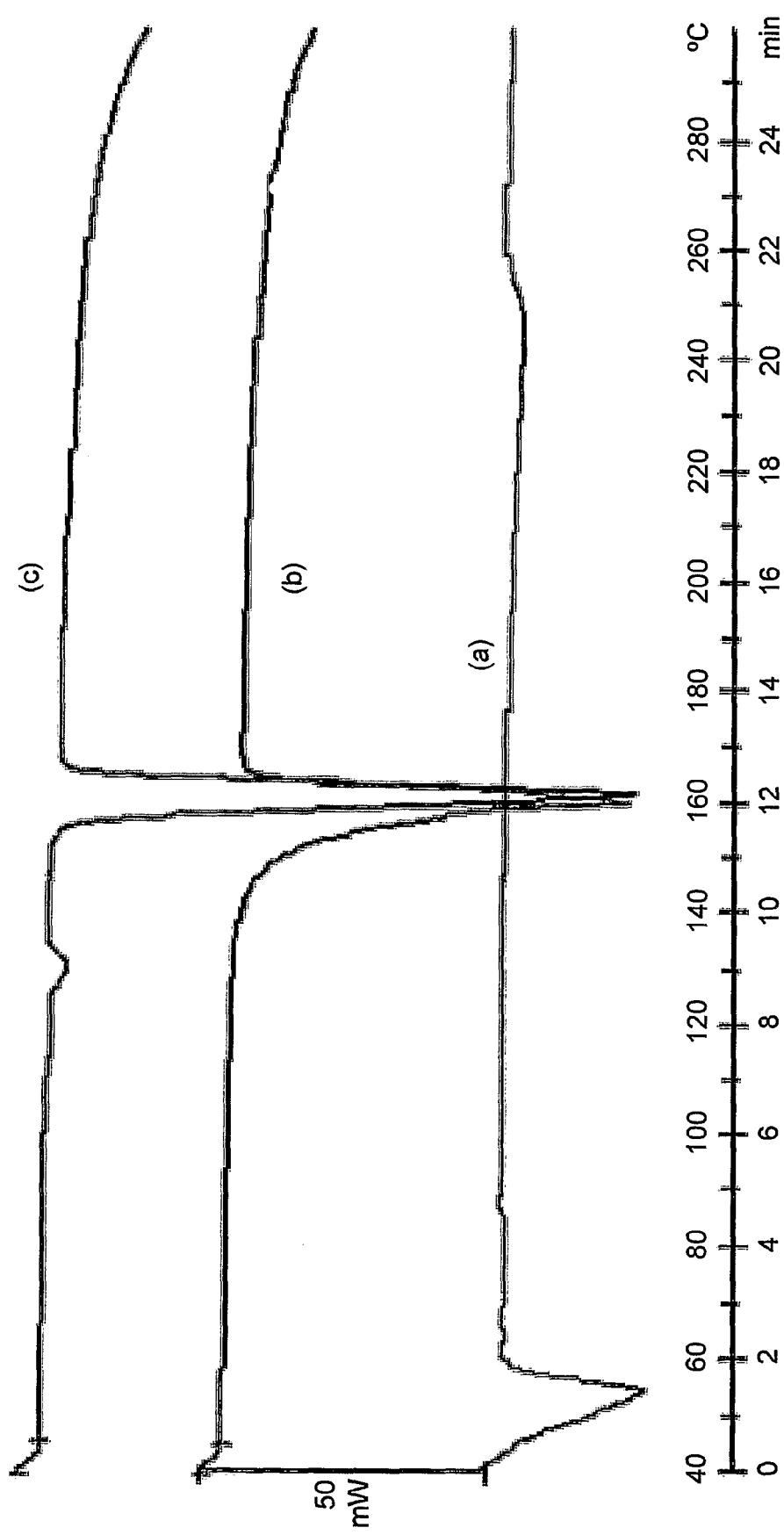
FIG. 7 shows the DSC traces of Propiconazole (a), Propiconazole-Isonicotinamide co-crystal (b) and Isonicotinamide (c)

FIG. 7: DSC traces of Propiconazole (a), Propiconazole-Isonicotinamide Co-Crystal (b) and Isonicotinamide (c).

Table 4: 2θ values of selected peak positions of the Powder X-Ray Diffraction patterns of Propiconazole-Isonicotinamide Co-Crystal.

TABLE 4

| PPZ - Isonicotinamide Co-Crystal 2θ |
| --- |
| 7.832 |
| 11.67 |
| 22.965 |
| 23.339 |
| 24.213 |
| 25.804 |
| 33.23 |

Experimental

For a 2:1 Co-Crystal by Cooling Crystallisation 2 g of PPZ was added to a 40 ml vial with 5 ml Isohexane.

1.5 g of Isonicotinamide in 5 ml Methanol was added to this mixture.

The sample was kept at 50° C. for 2 hours, then kept at 40° C. for an hour, then kept at 30° C. for an hour, and then finally kept at 20° C. for an hour, before being left overnight in the fridge. The product was then isolated on a Buchner.

4 Propiconazole-2,3,5,6-Tetrahydroxy-1,4-benzoquinone co-crystal

Figure 8:
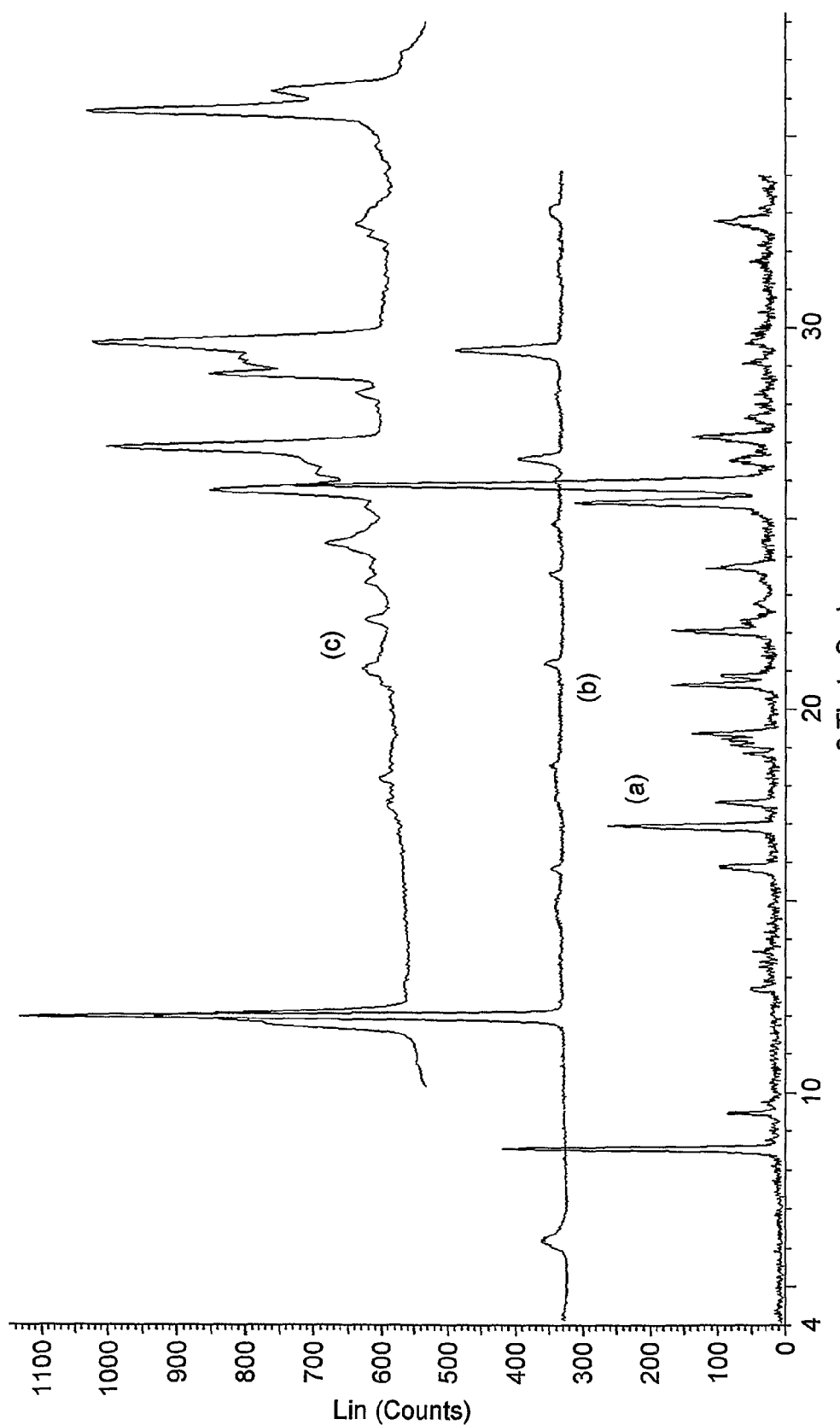
FIG. 8 shows the Powder X-Ray Diffraction patterns of Propiconazole (a), Propiconazole-2,3,5,6-Tetrahydroxy-1,4-benzoquinone co-crystal (b) and 2,3,5,6-Tetrahydroxy-1,4-benzoquinone (c)

FIG. 8: Powder X-Ray Diffraction patterns of Propiconazole (a), Propiconazole-2,3,5,6-Tetrahydroxy-1,4-benzoquinone Co-Crystal (b) and 2,3,5,6-Tetrahydroxy-1,4-benzoquinone (c).

Figure 9:
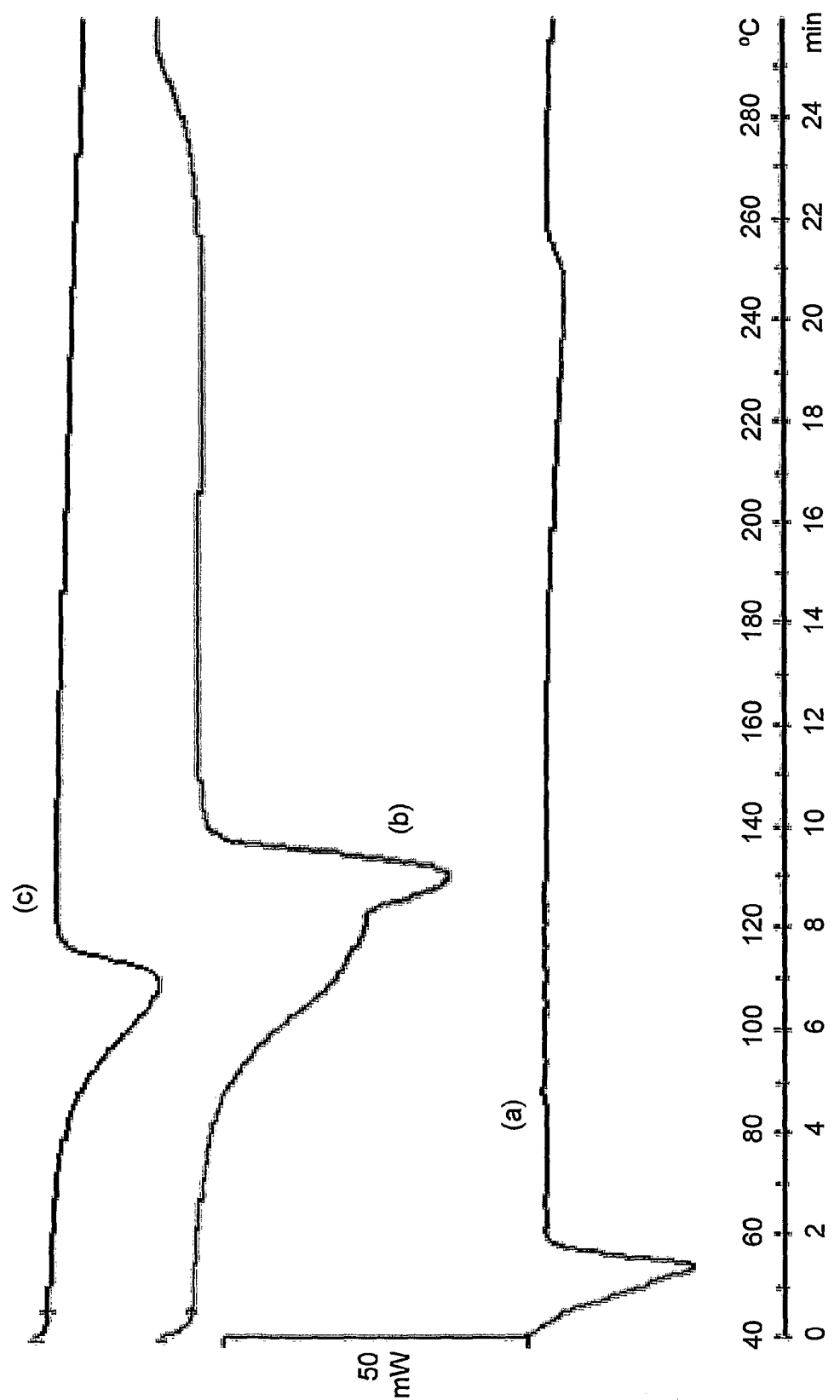
FIG. 9 shows the DSC traces of Propiconazole (a), Propiconazole-2,3,5,6-Tetrahydroxy-1,4-benzoquinone co-crystal (b) and 2,3,5,6-Tetrahydroxy-1,4-benzoquinone (c)

FIG. 9: DSC traces of Propiconazole (a), Propiconazole-2,3,5,6-Tetrahydroxy-1,4-benzoquinone Co-Crystal (b) and 2,3,5,6-Tetrahydroxy-1,4-benzoquinone (c).

Table 5: 2θ values of selected peak positions of the Powder X-Ray Diffraction patterns of Propiconazole-2,3,5,6-Tetrahydroxy-1,4-benzoquinone Co-Crystal.

TABLE 5

| PPZ - 2,3,5,6-Tetrahydroxy-1,4-benzoquinone Co-Crystal 2θ |
| --- |
| 6.131 |
| 11.946 |
| 15.835 |
| 21.23 |
| 23.577 |
| 24.908 |
| 26.625 |
| 29.462 |
| 33.141 |

Experimental

For a 1:2 Co-Crystal by Evaporative Crystallisation 1.286 g of PPZ was added to a 40 ml vial with 5 ml Acetone.

1.57 g of 2,3,5,6-Tetrahydroxy-1,4-benzoquinone in 5 ml Methanol was added to this mixture.

The sample was kept at 50° C. for 2 hours and then allowed to cool, and evaporate, before being filtered on a Buchner.

5 Propiconazole-5-Hydroxy-2-methylpyridine co-crystal

Figure 10:
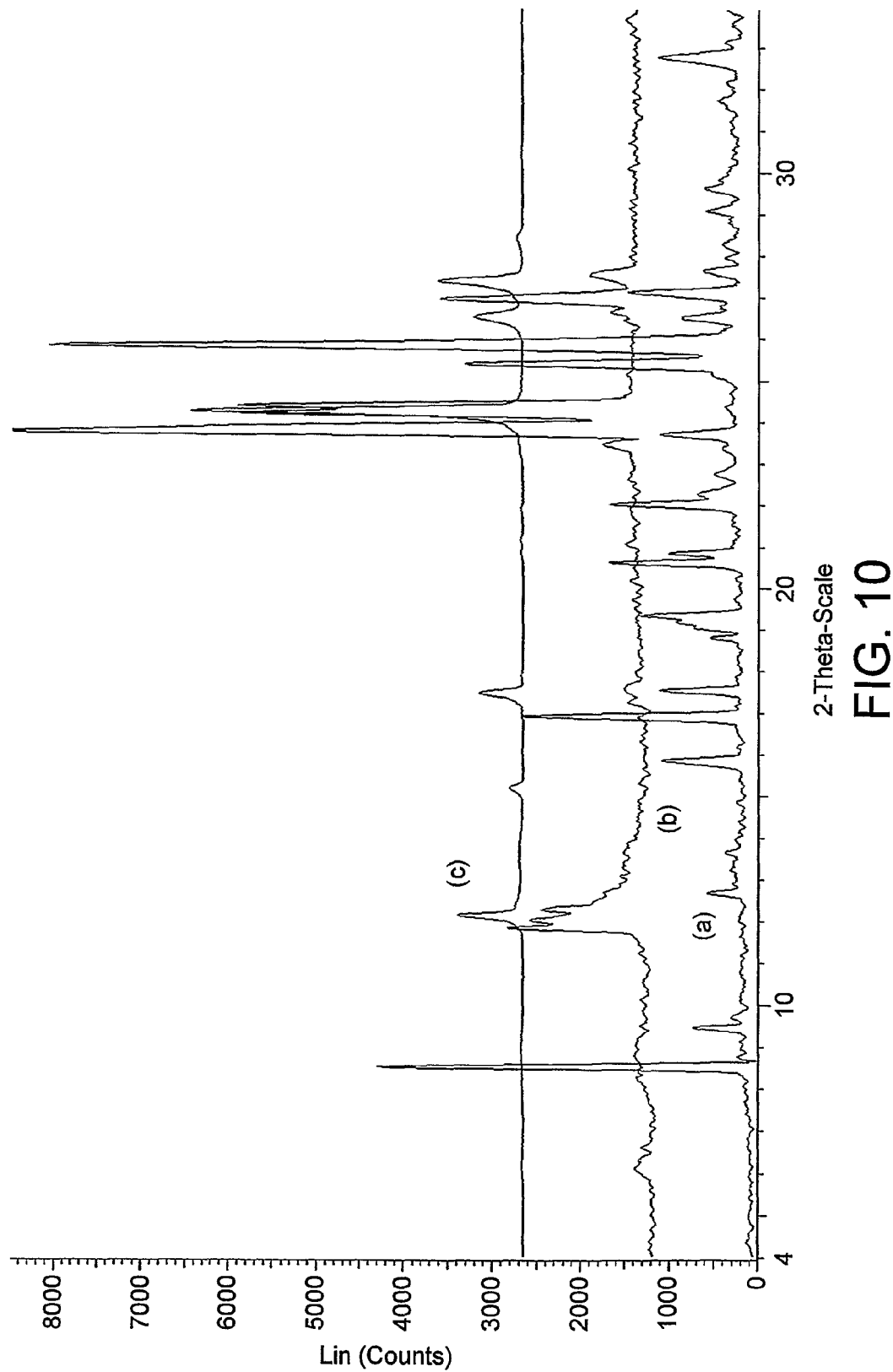
FIG. 10 shows the Powder X-Ray Diffraction patterns of Propiconazole (a), Propiconazole-5-Hydroxy-2-methylpyridine co-crystal (b) and 5-Hydroxy-2-methylpyridine (c)

FIG. 10: Powder X-Ray Diffraction patterns of Propiconazole (a), Propiconazole-5-Hydroxy-2-methylpyridine Co-Crystal (b) and 5-Hydroxy-2-methylpyridine (c).

Figure 11:
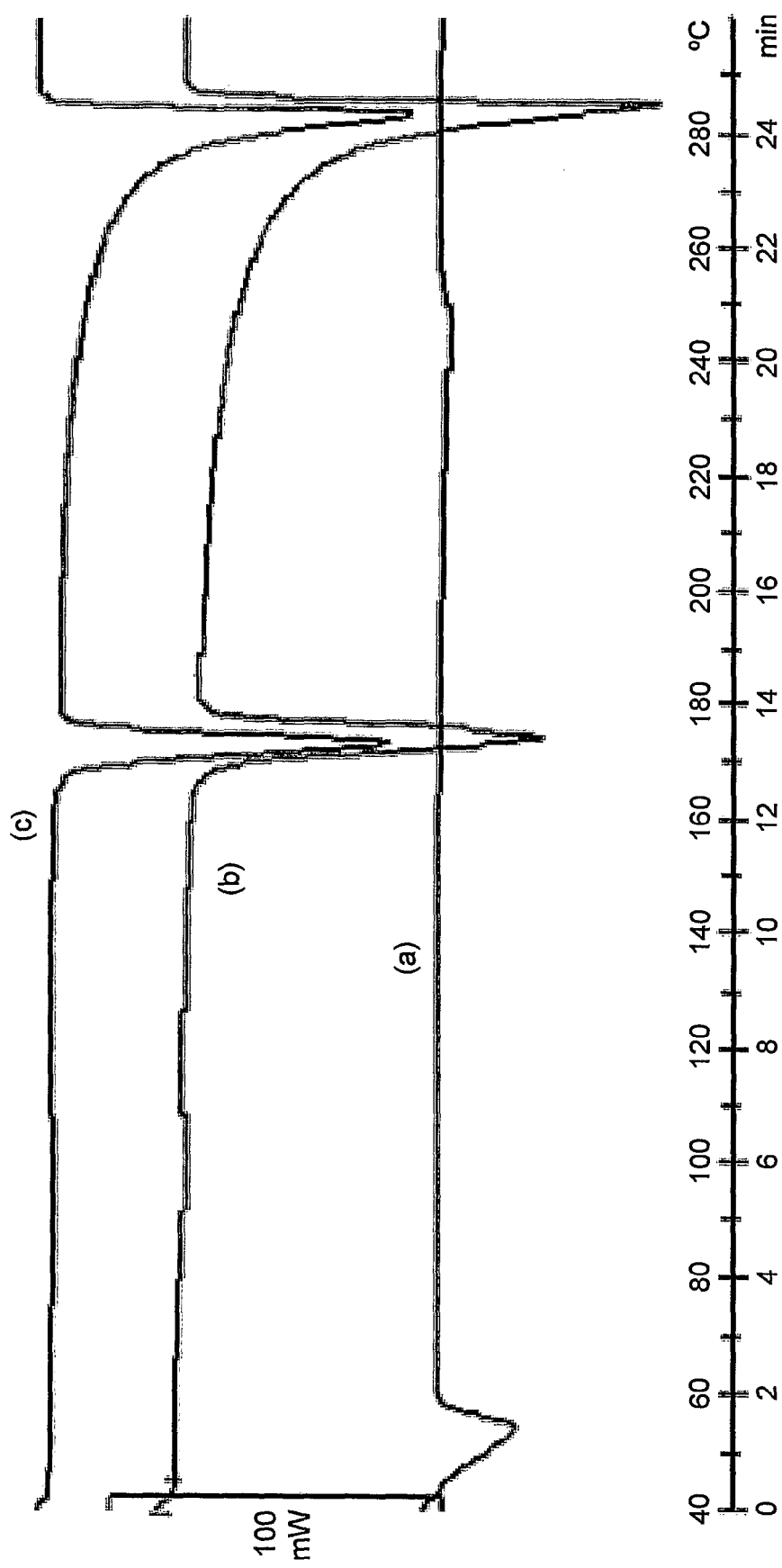
FIG. 11 shows the DSC traces of Propiconazole (a), Propiconazole-5-Hydroxy-2-methylpyridine co-crystal (b) and 5-Hydroxy-2-methylpyridine (c)

FIG. 11: DSC traces of Propiconazole (a), Propiconazole-5-Hydroxy-2-methylpyridine Co-Crystal (b) and 5-Hydroxy-2-methylpyridine (c).

Table 6: 2θ values of selected peak positions of the Powder X-Ray Diffraction patterns of Propiconazole-5-Hydroxy-2-methylpyridine Co-Crystal.

TABLE 6

| PPZ - 5-Hydroxy-2-methylpyridine Co-Crystal 2θ |
| --- |
| 6.119 |
| 11.777 |
| 12.023 |
| 12.238 |
| 17.526 |
| 23.492 |
| 23.799 |
| 24.23 |
| 24.445 |
| 26.659 |
| 26.966 |
| 27.55 |

Experimental

For a 2:1 Co-Crystal by Cooling Crystallisation 2 g of PPZ was added to a 40 ml vial with 5 ml Xylene.

1.3 g of 5-Hydroxy-2-methylpyridine in 5 ml Methanol was added to this mixture.

The sample was kept at 50° C. for 2 hours, then kept at 40° C. for an hour, then kept at 30° C. for an hour, and then finally kept at 20° C. for an hour, before being left overnight in the fridge. The product was then isolated on a Buchner.

6 Propiconazole-Nicotinamide co-crystal

Figure 12:
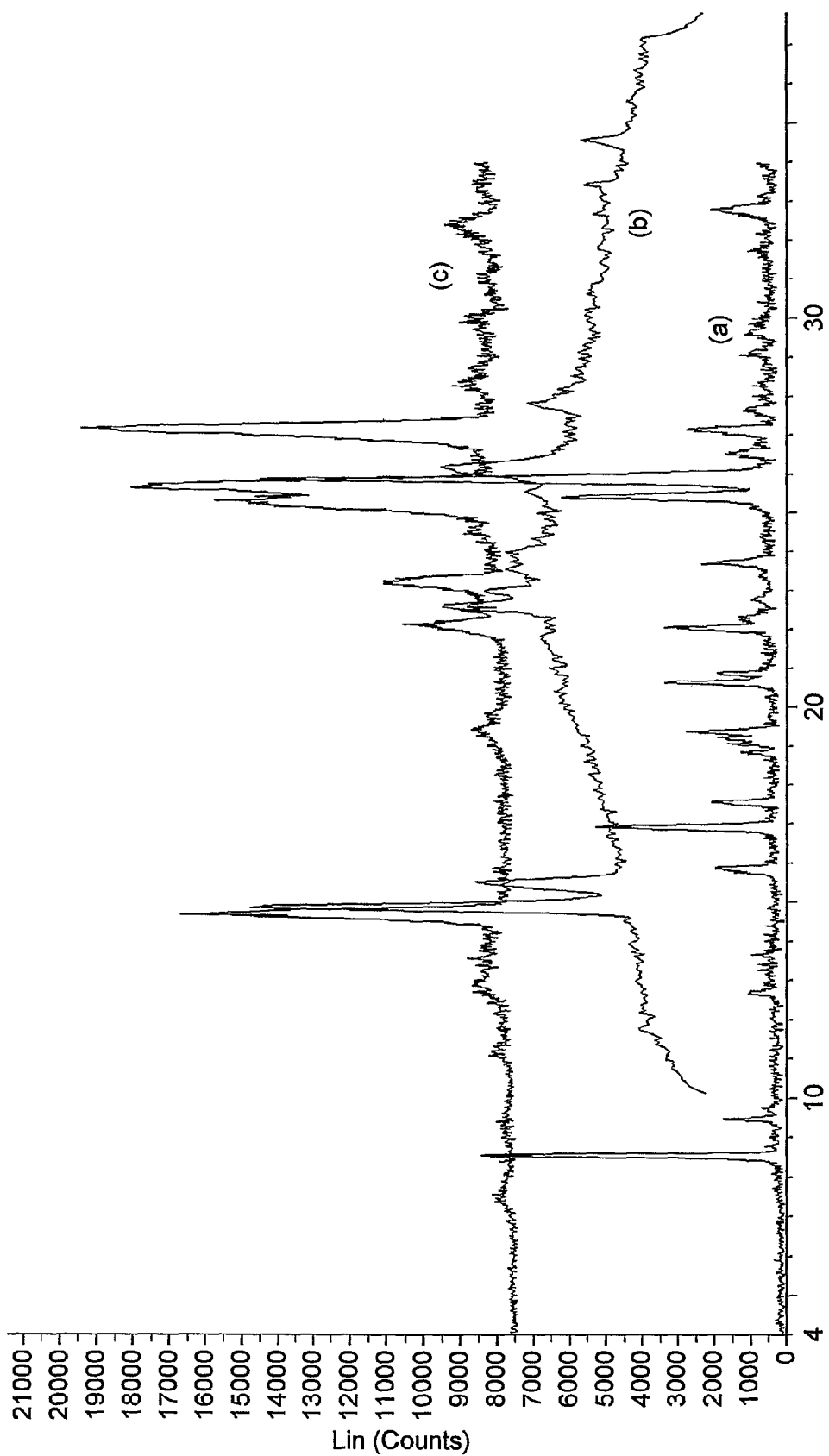
FIG. 12 shows the Powder X-Ray Diffraction patterns of Propiconazole (a), Propiconazole-Nicotinamide co-crystal (b) and Nicotinamide (c)

FIG. 12: Powder X-Ray Diffraction patterns of Propiconazole (a), Propiconazole-Nicotinamide Co-Crystal (b) and Nicotinamide (c).

Figure 13:
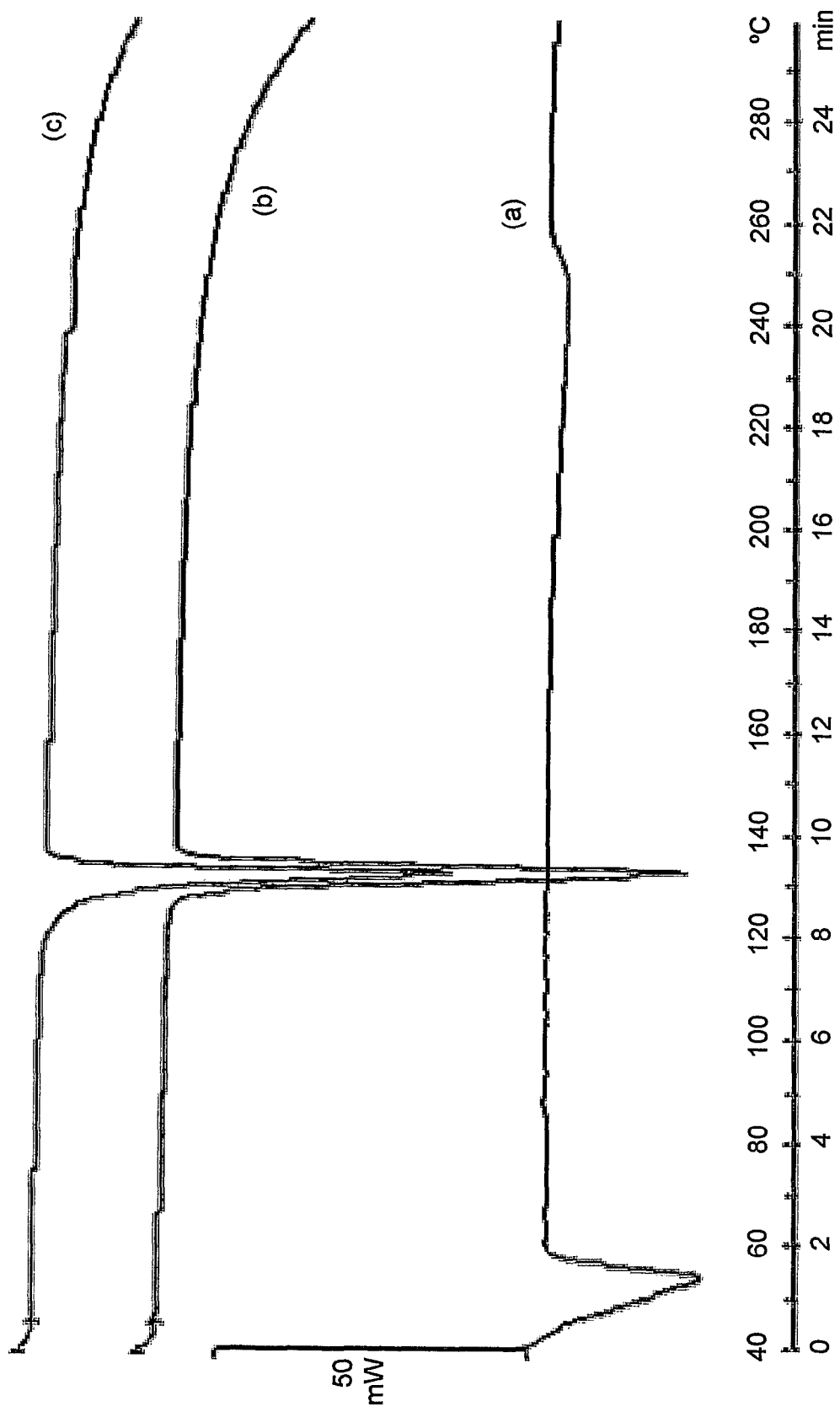
FIG. 13 shows the DSC traces of Propiconazole (a), Propiconazole-Nicotinamide co-crystal (b) and Nicotinamide (c)

FIG. 13: DSC traces of Propiconazole (a), Propiconazole-Nicotinamide Co-Crystal (b) and Nicotinamide (c).

Table 7: 2θ values of selected peak positions of the Powder X-Ray Diffraction patterns of Propiconazole-Nicotinamide Co-Crystal.

TABLE 7

| PPZ - Nicotinamide Co-Crystal 2θ |
| --- |
| 14.875 |
| 15.499 |
| 22.608 |
| 23.024 |
| 23.509 |
| 24.029 |
| 25.52 |
| 26.179 |
| 27.843 |
| 33.495 |
| 34.605 |

Experimental

For a 2:1 Co-Crystal by Cooling Crystallisation 2 g of PPZ was added to a 40 ml vial with 5 ml Acetone.

1.3 g of Nicotinamide in 5 ml Ethyl acetate was added to this mixture.

The sample was kept at 50° C. for 2 hours, then kept at 40° C. for an hour, then kept at 30° C. for an hour, and then finally kept at 20° C. for an hour, before being left overnight in the fridge. The product was then isolated on a Buchner.

7 Propiconazole-Methyl hydrazino carboxylate co-crystal

Figure 14:
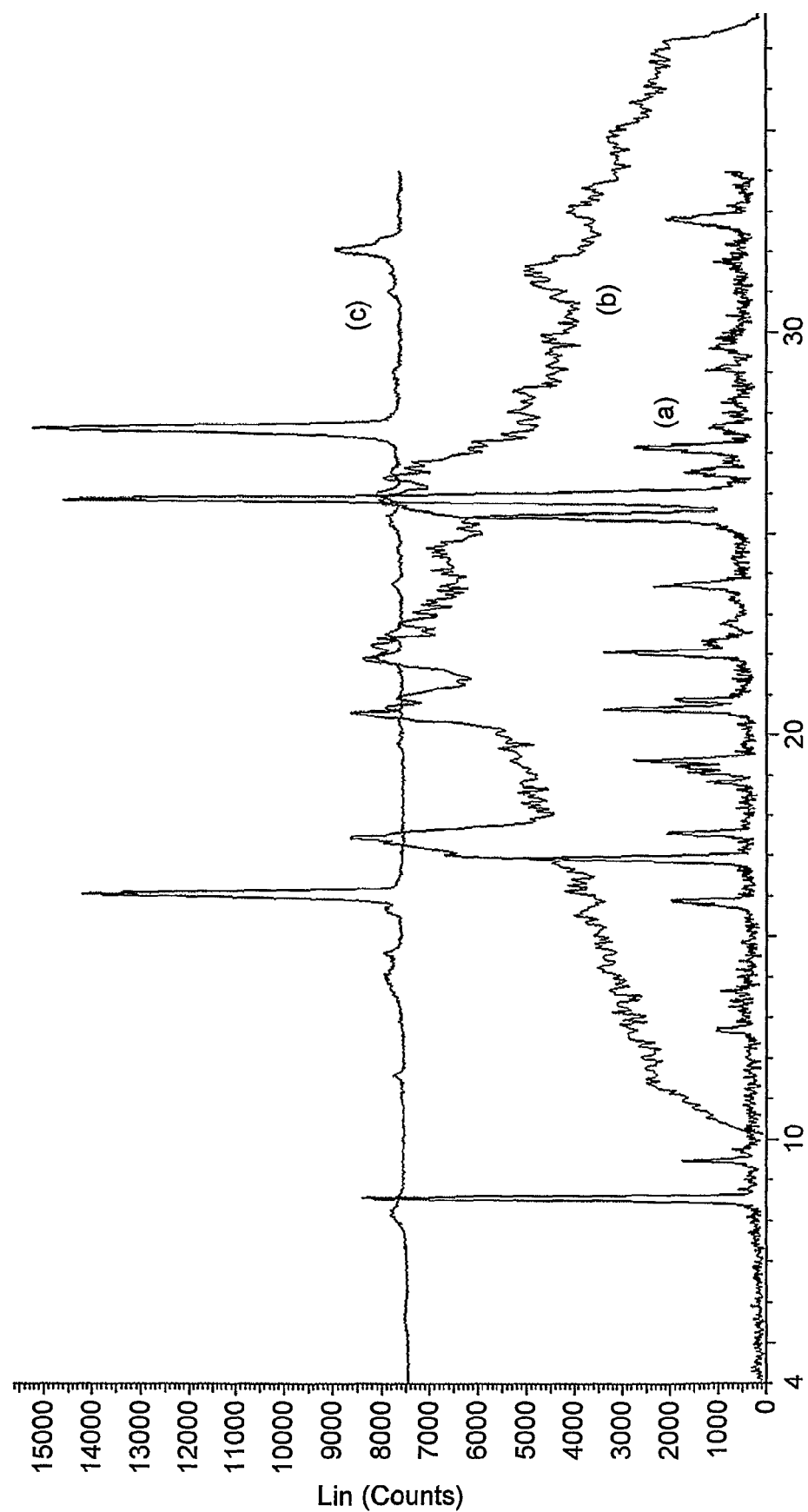
FIG. 14 shows the Powder X-Ray Diffraction patterns of Propiconazole (a), Propiconazole-Methyl hydrazinocarboxylate co-crystal (b) and Methyl hydrazino carboxylate (c)

FIG. 14: Powder X-Ray Diffraction patterns of Propiconazole (a), Propiconazole-Methyl hydrazino carboxylate Co-Crystal (b) and Methyl hydrazino carboxylate (c).

Table 8: 2θ values of selected peak positions of the Powder X-Ray Diffraction patterns of Propiconazole-Methyl hydrazino carboxylate Co-Crystal.

TABLE 8

| PPZ - Methyl hydrazino carboxylate Co-Crystal 2θ |
| --- |
| 17.447 |
| 20.5 |
| 21.922 |
| 24.662 |
| 25.807 |
| 26.396 |
| 28.547 |
| 31.53 |
| 32.987 |

Experimental

For a 1:2 Co-Crystal by Cooling Crystallisation 0.5 g of PPZ was added to a 40 ml vial with 5 ml Acetone.

3.8 g of Methyl hydrazino carboxylate in 5 ml Methanol was added to this mixture.

The sample was kept at 50° C. for 2 hours, then kept at 40° C. for an hour, then kept at 30° C. for an hour, and then finally kept at 20° C. for an hour, before being left overnight in the fridge. The product was then isolated on a Buchner.

8. Propiconazole-4(3H)-Pyrimidinone co-crystal

Figure 15:
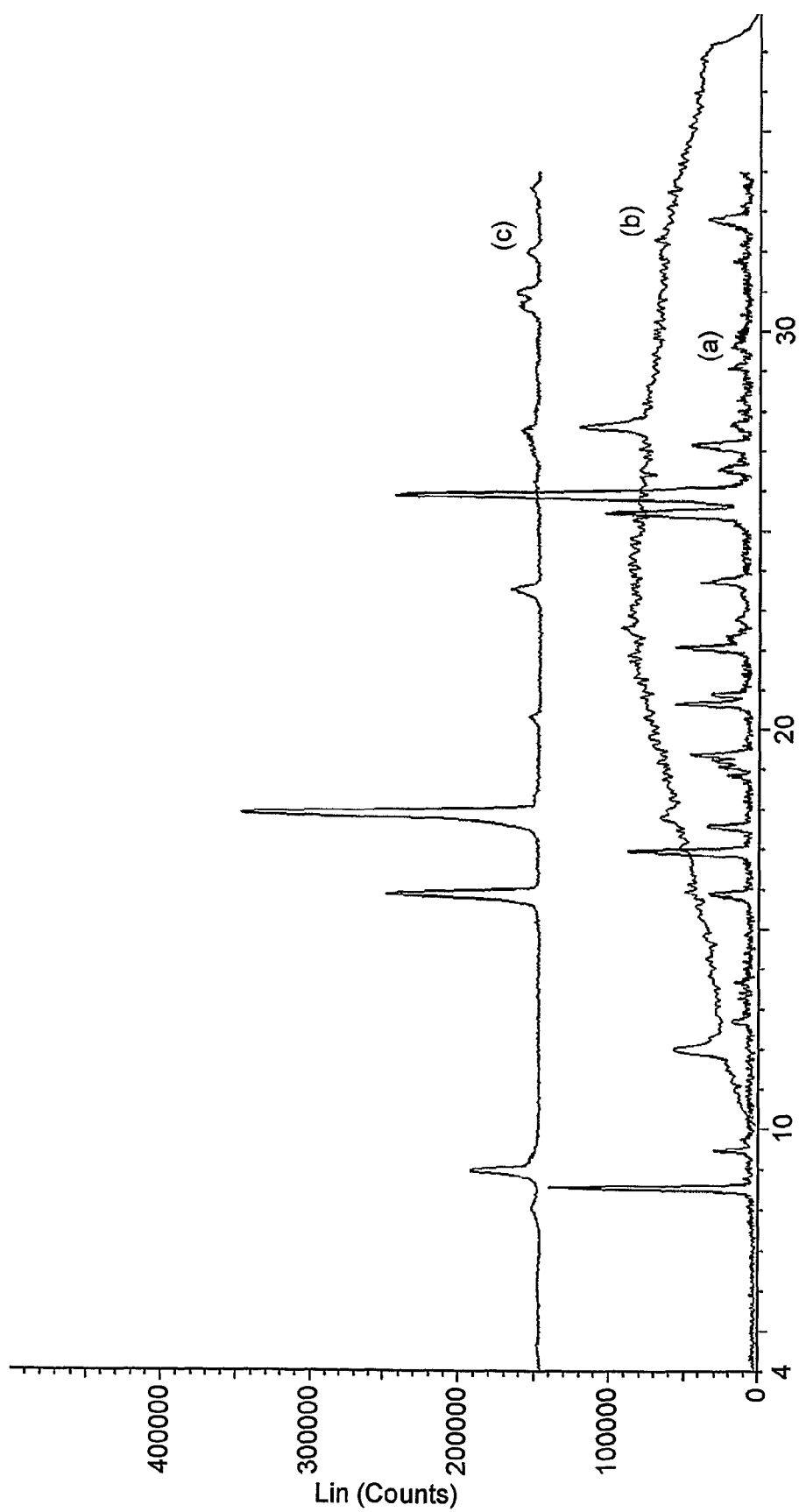
FIG. 15 shows the Powder X-Ray Diffraction patterns of Propiconazole (a), Propiconazole-4(3H)-Pyrimidinone co-crystal (b) and 4(3H)-Pyrimidinone (c)

FIG. 15: Powder X-Ray Diffraction patterns of Propiconazole (a), Propiconazole-4(3H)-Pyrimidinone Co-Crystal (b) and 4(3H)-Pyrimidinone (c).

Table 9: 2θ values of selected peak positions of the Powder X-Ray Diffraction patterns of Propiconazole-4(3H)-Pyrimidinone Co-Crystal.

| PPZ - 4(3H)-Pyrimidinone Co-Crystal 2θ |
|---|
| 11.922 |
| 15.85 |
| 16.997 |
| 17.761 |
| 27.632 |
| 32.325 |

Experimental

For a 1:1 Co-Crystal by Evaporative Crystallisation 0.5 g of PPZ was added to a 40 ml vial with 5 ml Acetone. 1.8 g of 4(3H)-Pyrimidinone in 5 ml Methanol was added to this mixture.

The sample was kept at 50° C. for 2 hours and then allowed to cool, and evaporate, before being filtered on a Buchner.

9 Propiconazole-15-Hydroxypentadecanoic acid co-crystal

Figure 16:
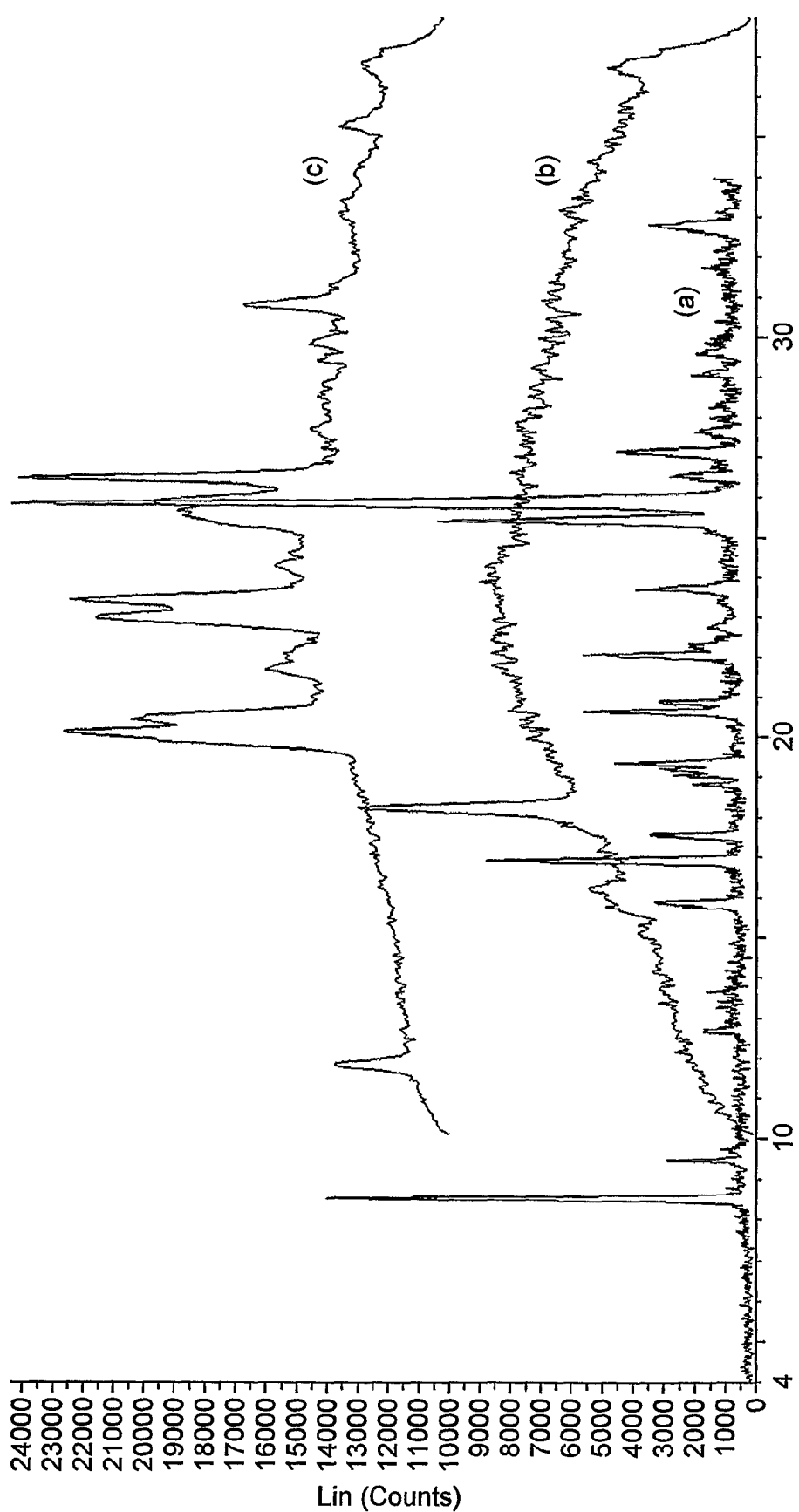
FIG. 16 shows the Powder X-Ray Diffraction patterns of Propiconazole (a), Propiconazole-15-Hydroxypentadecanoic acid co-crystal (b) and 15-Hydroxypentadecanoic acid (c)

FIG. 16: Powder X-Ray Diffraction patterns of Propiconazole (a), Propiconazole-15-Hydroxypentadecanoic acid Co-Crystal (b) and 15-Hydroxypentadecanoic acid (c).

Table 10: 2θ values of selected peak positions of the Powder X-Ray Diffraction patterns of Propiconazole-15-Hydroxypentadecanoic acid Co-Crystal.

| PPZ - 15-Hydroxypentadecanoic acid Co-Crystal 2θ |
|---|
| 16.232 |
| 18.178 |
| 33.228 |

Experimental

For a 2:1 Co-Crystal by Cooling Crystallisation 2 g of PPZ was added to a 40 ml vial with 5 ml Acetone. 1.3 g of 15-Hydroxypentadecanoic acid in 5 ml Ethyl acetate was added to this mixture.

The sample was kept at 50° C. for 2 hours, then kept at 40° C. for an hour, then kept at 30° C. for an hour, and then finally kept at 20° C. for an hour, before being left overnight in the fridge. The product was then isolated on a Buchner.

10 Propiconazole-Urea co-crystal

Figure 17:
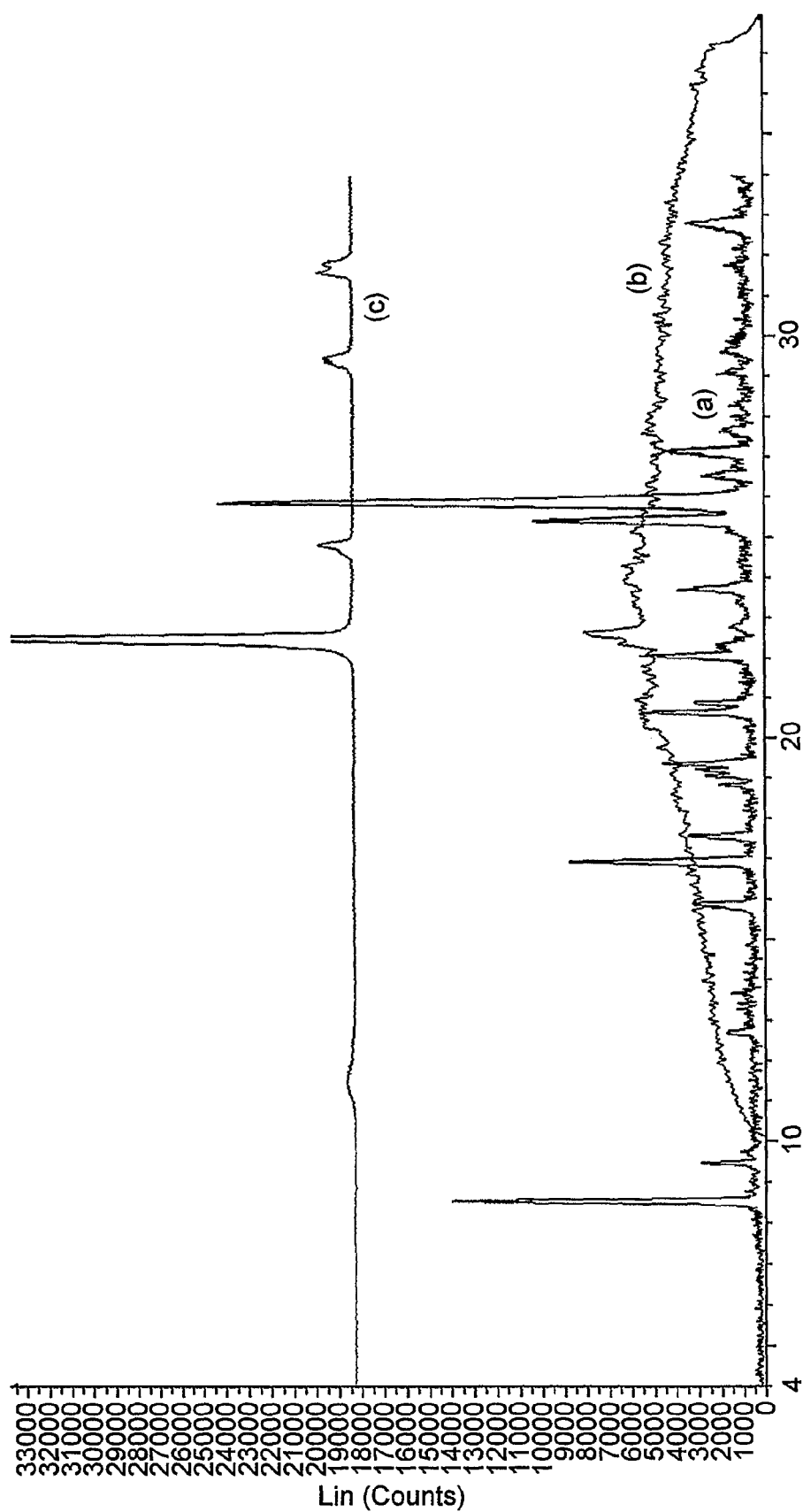
FIG. 17 shows the Powder X-Ray Diffraction patterns of Propiconazole (a), Propiconazole-Urea co-crystal (b) and Urea (c)

FIG. 17: Powder X-Ray Diffraction patterns of Propiconazole (a), Propiconazole-Urea Co-Crystal (b) and Urea (c).

Table 11: 2θ values of selected peak positions of the Powder X-Ray Diffraction patterns of Propiconazole-Urea Co-Crystal.

| PPZ - Urea Co-Crystal 2θ |
|---|
| 20.7 |
| 22.6 |
| 24.0 |
| 27.7 |

Experimental

For a 1:2 Co-Crystal by Cooling Crystallisation 0.5 g of PPZ was added to a 40 ml vial with 5 ml Acetone. 2.8 g of Urea in 5 ml Isohexane was added to this mixture.

The sample was kept at 50° C. for 2 hours, then kept at 40° C. for an hour, then kept at 30° C. for an hour, and then finally kept at 20° C. for an hour, before being left overnight in the fridge. The product was then isolated on a Buchner.

11 Propiconazole-1,9-Nonanediol acid co-crystal

Figure 18:
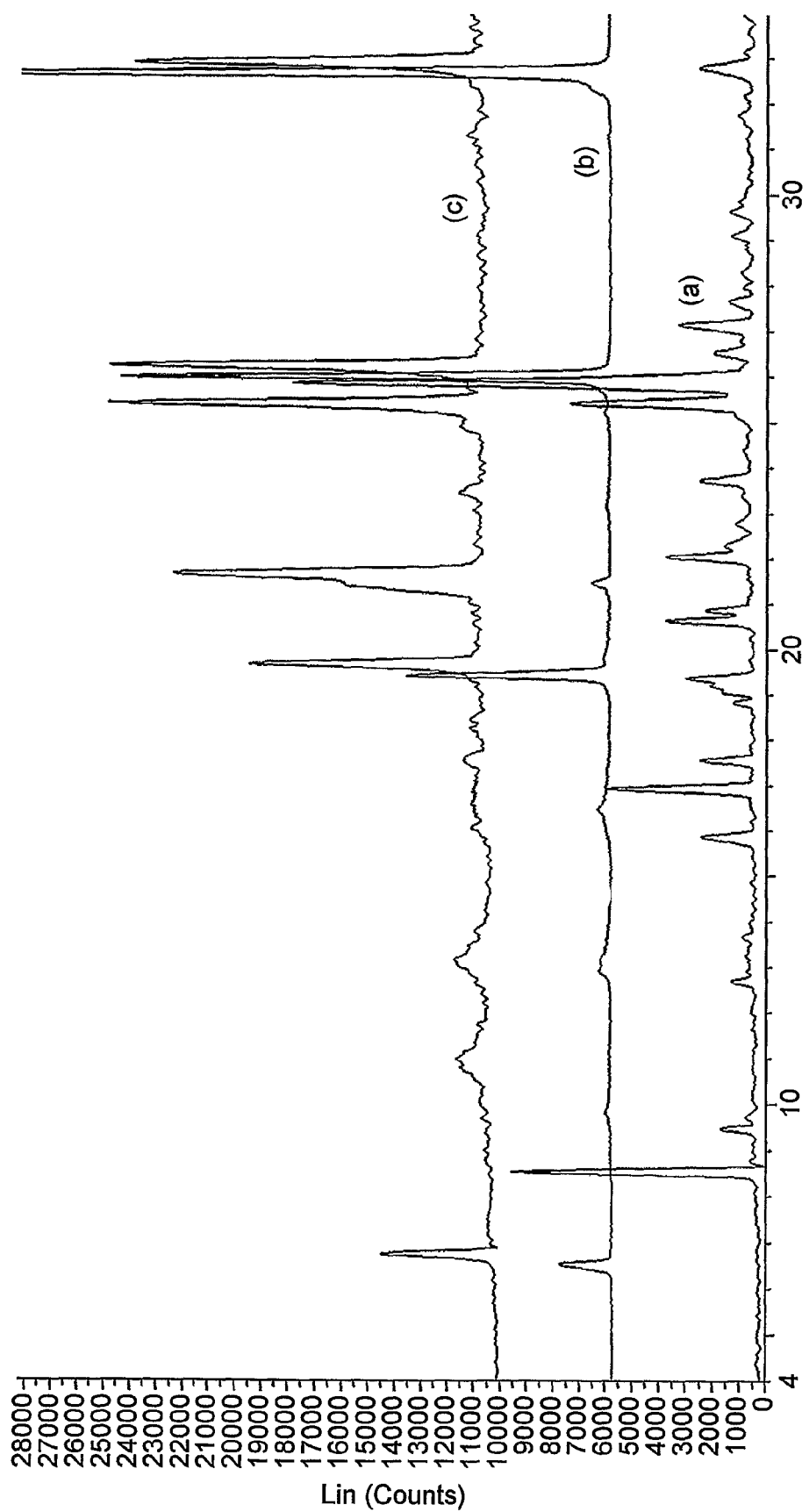
FIG. 18 shows the Powder X-Ray Diffraction patterns of Propiconazole (a), Propiconazole-1,9-Nonanediol co-crystal (b) and 1,9-Nonanediol(c)

FIG. 18: Powder X-Ray Diffraction patterns of Propiconazole (a), Propiconazole-1,9-Nonanediol Co-Crystal (b) and 1,9-Nonanediol(c).

Table 12: 2θ values of selected peak positions of the Powder X-Ray Diffraction patterns of Propiconazole-1,9-Nonanediol acid Co-Crystal.

| PPZ - 1,9-Nonanediol Co-Crystal 2θ |
|---|
| 10.406 |
| 12.461 |
| 13.783 |
| 15.533 |
| 17.068 |
| 20.659 |
| 24.404 |
| 27.229 |

Experimental

For a 2:1 Co-Crystal by Cooling Crystallisation 2 g of PPZ was added to a 40 ml vial with 5 ml Isohexane. 1.9 g of 1,9-Nonanediol in 5 ml Ethanol was added to this mixture.

The sample was kept at 50° C. for 2 hours and then allowed to cool, and evaporate, before being filtered on a Buchner.

12 Propiconazole-2-Hydroxy-6-methylpyridine co-crystal

Figure 19:
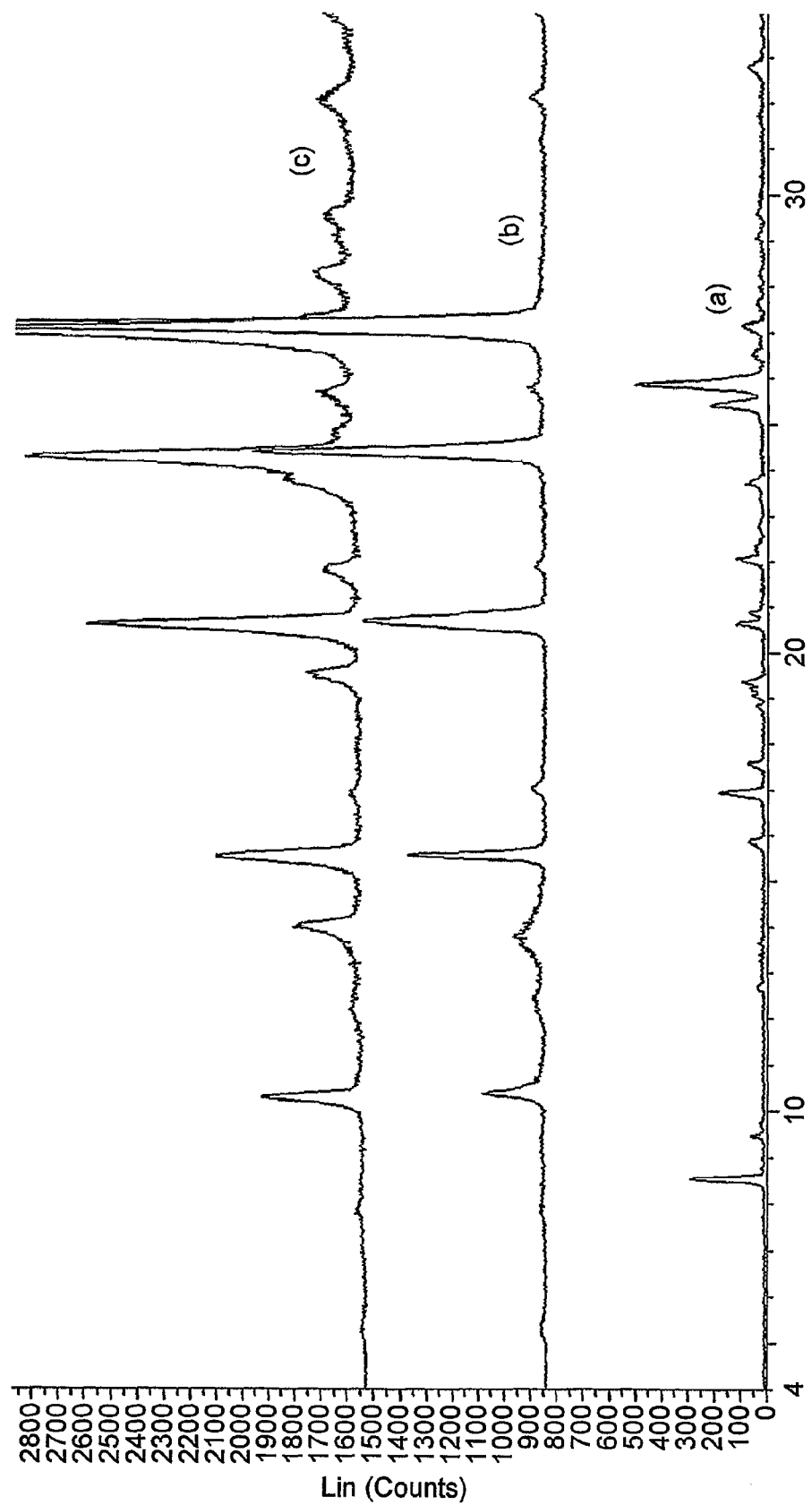
FIG. 19 shows the Powder X-Ray Diffraction patterns of Propiconazole (a), Propiconazole-2-Hydroxy-6-methylpyridine co-crystal (b) and 2-Hydroxy-6-methylpyridine (c).

FIG. 19: Powder X-Ray Diffraction patterns of Propiconazole (a), Propiconazole-2-Hydroxy-6-methylpyridine Co-Crystal (b) and 2-Hydroxy-6-methylpyridine (c).

Table 13: 2θ values of selected peak positions of the Powder X-Ray Diffraction patterns of Propiconazole-2-Hydroxy-6-methylpyridine Co-Crystal.

| PPZ - 2-Hydroxy-6-methylpyridine Co-Crystal 2θ |
|---|
| 6.537 |
| 9.851 |
| 12.951 |
| 16.511 |
| 19.396 |
| 21.421 |

| PPZ - 2-Hydroxy-6-methylpyridine Co-Crystal |
| --- |
| 2θ |
| 25.196 |
| 26.025 |
| 32.653 |

Experimental

For a 1:2 Co-Crystal by Evaporative Crystallisation 2 g of PPZ was added to a 40 ml vial with 5 ml Acetonitrile.

0.7 g of 2-Hydroxy-6-methylpyridine (5% in Ethanol) was added to this mixture.

The sample was kept at 50° C. for 2 hours and then allowed to cool, and evaporate, before being filtered on a Buchner.

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims. All publications cited herein are hereby incorporated by reference in their entirety for all purposes to the same extent as if each individual publication were specifically and individually indicated to be so incorporated by reference.

The invention claimed is:

1. A co-crystal of propiconazole with a co-crystal forming compound, wherein the co-crystal forming compound is selected from the group comprising 1,9-nonane diol, 2,3,5,6-tetrahydroxybenzoquinone, 15-hydroxypentadecanoic acid, 5-hydroxy-2-methylpyridine, 2-hydroxy-6-methylpyridine, nicotinamide, isonicotinamide, 4-(3H)-pyrimidinone, methyl hydrazinocarboxylate, 4,4'-dihydroxybiphenyl or 4,4-dihydroxy cyclohexylidine bisphenol.

2. The co-crystal of claim 1, wherein the co-crystal forming compound is 2,3,5,6-tetrahydroxybenzoquinone.

3. The co-crystal of claim 1, wherein the co-crystal forming compound is 5-hydroxy-2-methylpyridine.

4. The co-crystal of claim 1, wherein the co-crystal forming compound is nicotinamide.

5. The co-crystal of claim 1, wherein the co-crystal forming compound is isonicotinamide.

6. The co-crystal of claim 1, wherein the co-crystal forming compound is 4,4'-dihydroxybiphenyl.

7. The co-crystal of claim 1, wherein the co-crystal forming compound is 4,4-dihydroxy cyclohexylidine bisphenol.

8. A process of preparing a co-crystal of claim 1, said process comprising:
    grinding, heating or contacting, in solution, propiconazole with the co-crystal forming compound, under crystallisation conditions, so as to form a solid phase; and
    isolating co-crystals comprising propiconazole and the co-crystal forming compound.

9. A fungicidal composition comprising the co-crystal of claim 1.

10. A method of preventing/controlling fungal infection on plants comprising treating the plant with a fungicidally effective amount of an agricultural composition of claim 9.

11. An agrochemical formulation comprising the composition of claim 9 which is a suspension concentrate.

12. An agrochemical composition comprising the co-crystal of claim 1.

* * * * *